United States Patent [19]

Sato et al.

[11] 4,233,161
[45] Nov. 11, 1980

[54] SUBLIMABLE COMPOSITION

[75] Inventors: Haruhito Sato; Hiroshi Ichikawa; Hiroshi Hayashi; Konomu Kurisaki, all of Chiba, Japan

[73] Assignee: Idemitsu Kosan Company Limited, Tokyo, Japan

[21] Appl. No.: 862,620

[22] Filed: Dec. 20, 1977

[30] Foreign Application Priority Data

| Dec. 25, 1976 | [JP] | Japan | 51-155650 |
| Dec. 25, 1976 | [JP] | Japan | 51-155652 |
| Mar. 30, 1977 | [JP] | Japan | 52-34674 |
| May 21, 1977 | [JP] | Japan | 52-58220 |
| May 24, 1977 | [JP] | Japan | 52-59360 |
| May 27, 1977 | [JP] | Japan | 52-61255 |
| Jun. 7, 1977 | [JP] | Japan | 52-66298 |

[51] Int. Cl.³ .................... C09K 3/00; A61K 7/46
[52] U.S. Cl. .................... 252/1; 239/60; 252/384; 252/399; 252/407; 252/522 A; 424/219; 424/308; 424/324; 424/333; 424/343; 424/346; 424/DIG. 10
[58] Field of Search ............ 239/60; 252/1, 384, 252/399, 407, 522 A; 260/666 M, 666 P, 666 PY; 424/219, DIG. 10, 308, 324, 333, 343, 346

[56] References Cited

U.S. PATENT DOCUMENTS

| 1,685,624 | 9/1928 | Andrews | 260/706 X |
| 2,105,911 | 1/1938 | Foster | 260/706 X |
| 3,128,316 | 4/1964 | Schneider | 260/666 M |
| 3,258,498 | 1/1966 | Schneider | 260/666 M |
| 3,781,428 | 12/1973 | Hennart et al. | 239/60 X |
| 3,988,354 | 10/1976 | Mazrov et al. | 260/706 |

FOREIGN PATENT DOCUMENTS

| 3920737 | 9/1964 | Japan . | |
| 142902 | 5/1920 | United Kingdom | 260/706 |
| 1447653 | 8/1976 | United Kingdom . | |

Primary Examiner—Leland A. Sebastian
Attorney, Agent, or Firm—Frishauf, Holtz, Goodman & Woodward

[57] ABSTRACT

A sublimable composition comprising sublimable hydrocarbons and sublimable polar compounds, which is useful as a carrier for perfume, a mothproofing agent, a deodorant, and the like; a process for producing a molding from the above composition; and a sublimable multilayer molding.

19 Claims, 23 Drawing Figures

FIG. 17A      CARRIER: ADAMANTANE-TMN
• PERFUME
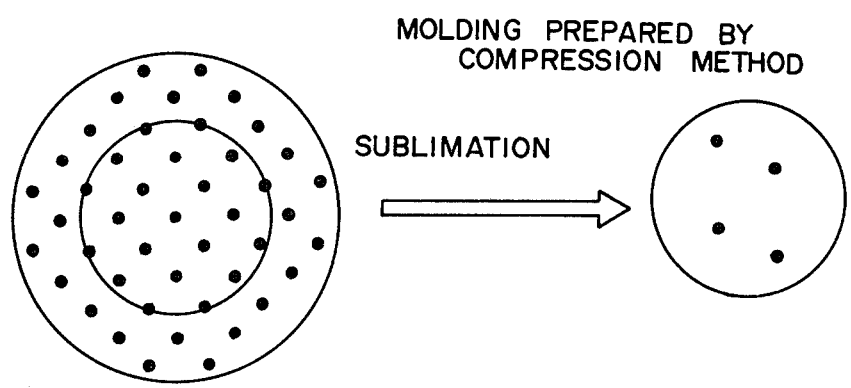
MOLDING PREPARED BY COMPRESSION METHOD
SUBLIMATION
FIG. 17B      MOLDING PREPARED BY MELTING METHOD
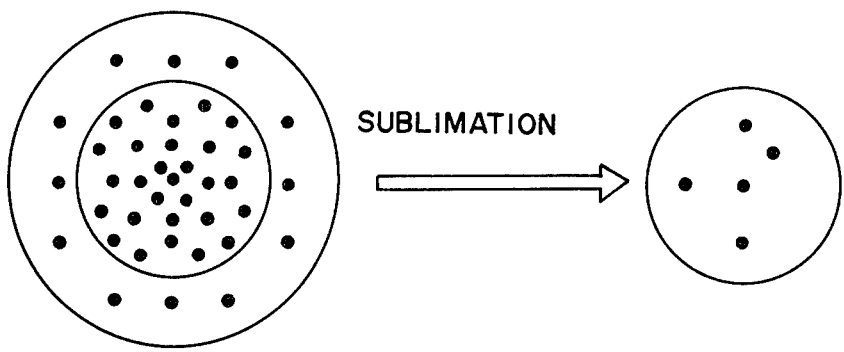
SUBLIMATION

FIG.18A
CARRIER: ADAMANTANE-TMN-DIMETHYL FUMARATE
● : PERFUME
⬡ : DIMETHYL FUMARATE
MOLDING PREPARED BY COMPRESSION METHOD
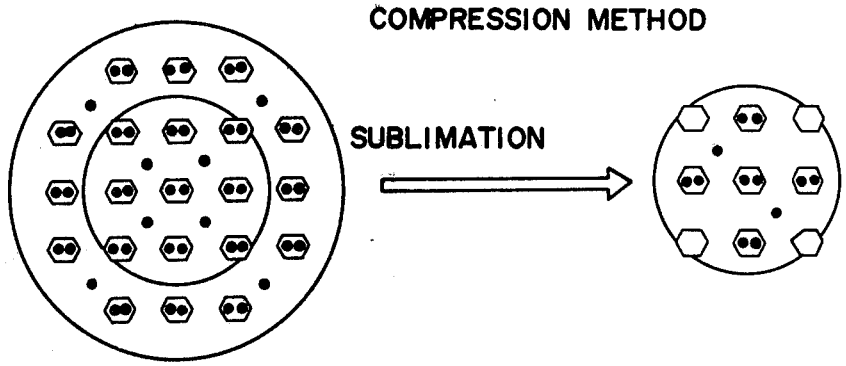
FIG.18B  MOLDING PREPARED BY MELTING METHOD
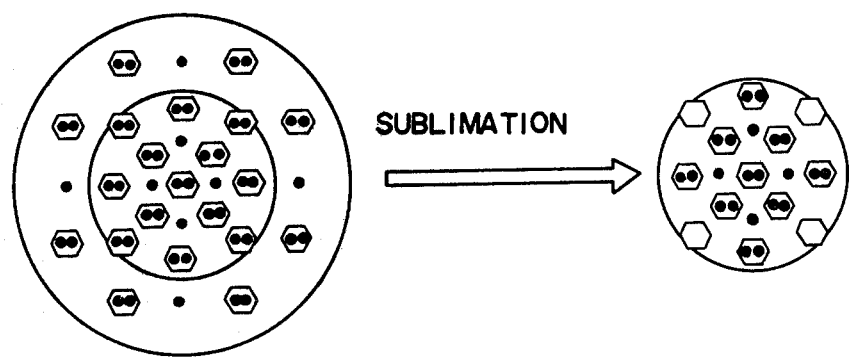

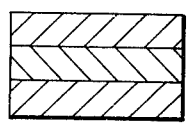
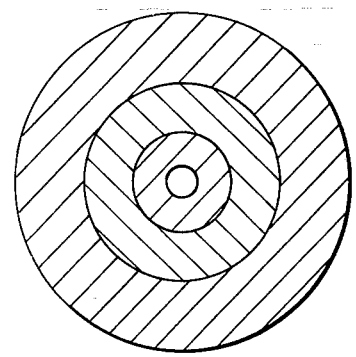
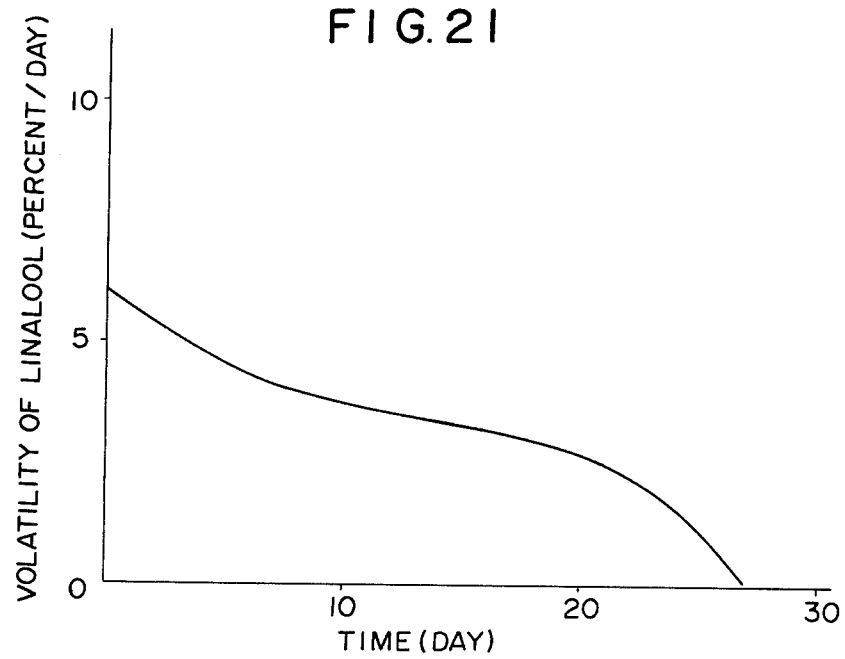

SUBLIMABLE COMPOSITION

BACKGROUND OF THE INVENTION

1. Field of the Invention

This invention relates to sublimable compositions. More particularly, it relates to sublimable compositions comprising sublimable hydrocarbons such as adamantane and sublimable polar compounds, and if necessary, containing effective components and antioxidants, processes for producing moldings from the sublimable compositions, and sublimable multi-layer moldings.

2. Description of the Prior Art

As carrier for retaining effective components such as perfume, mothproofing agent, deodorants, preservative and the like, non-volatile supporters such as agar gel, polyacrylamide and the like or sublimable carriers and the like have hitherto been known. With the non-volatile carriers, however, it is difficult to continue volatilizing constantly the effective components for a long period of time since the effective components contained in the non-valatile supporters volatilize as the carriers themselves dry spontaneously. Furthermore, they have the disadvantage that water oozes out from a molding formed of the non-volatile carrier. Sublimable carriers widely employed include camphor, naphthalene, para-dichlorobenzene and the like. These sublimable carriers, however, have their characteristic odors, providing a irritating and unpleasant feeling. Furthermore, it is difficult to provide desired perfume to the sublimable carriers.

Thus it has long been desired to obtain sublimable compositions which can be employed as excellent carriers capable of retaining a large amount of effective components such as perfume and the like for a long period of time. The term "carrier" used in this invention designates a part of the composition subtracting effective components from it.

SUMMARY OF THE INVENTION

It has now been found that those compositions comprising sublimable hydrocarbons such as adamantane and sublimable polar compounds can retain a large amount of effective components for a long period of time.

Thus the present invention provides sublimable compositions comprising sublimable hydrocarbons and sublimable polar compounds.

BRIEF DESCRIPTION OF THE DRAWINGS

FIG. 17 is a model showing the relation between the sublimation of a carrier and the volatility of perfume;

FIG. 18 is a model showing the volatility characteristics of perfume where another carrier is employed;

FIGS. 19 and 20 are sectional views of various embodiments of moldings of this invention;

FIG. 21 shows a change with time in the volatility ratio of linallol of Example 28;

DETAILED DESCRIPTION OF THE INVENTION

Figure 1:
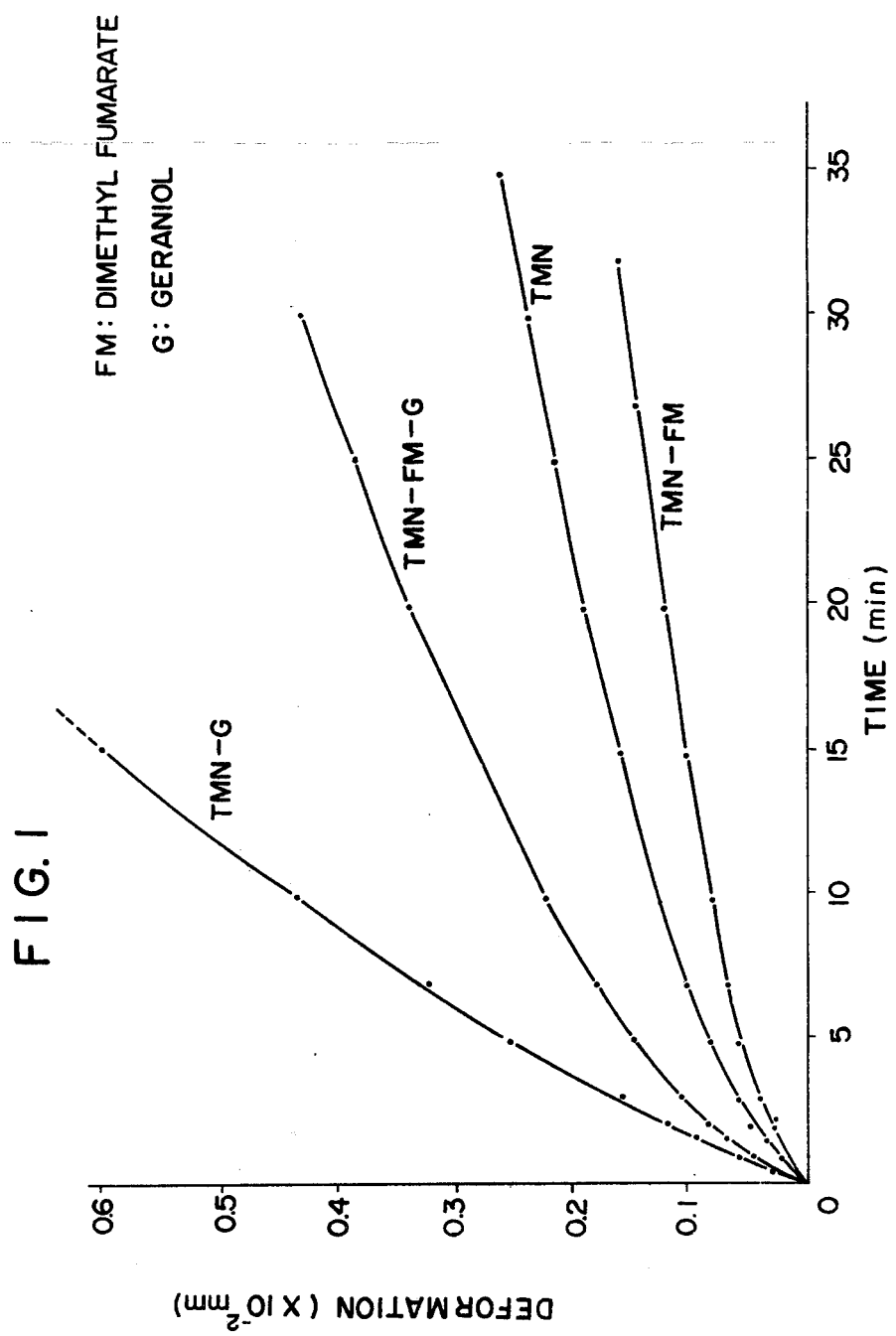
FIGS. 1 and 2 are graphs showing the creep characteristics and the perfume retention ratio of the composition of this invention respectively.

Sublimable hydrocarbons which can be used in this invention, include adamantane, endo-trimethylenenorbornane (hereinafter referred to merely as TMN), cyclododecane (hereinafter referred to merely as CD), trimethylnorbornane, norbornane, naphthalene, and the like. These sublimable hydrocarbons principally play a part in controlling the sublimation rate of the whole of a composition. These sublimable hydrocarbons except for adamantane, however, when used singly can usually retain only one percent by weight or less of effective components such as a perfume and the like, and furthermore their abilities to retain the effective components are insufficient. Thus it is required that these sublimable hydrocarbons are used in combination with sublimable polar compounds.

Combined use of sublimable hydrocarbons and sublimable polar compounds enables the retention ratio of effective components in the carrier to markedly increase owing to their mutual interaction.

As the sublimable polar compounds used in combination with the sublimable hydrocarbons, those materials are used which are little compatible with the sublimable hydrocarbons at ordinary temperature. Sublimable polar compounds which can be used in this invention, include dimethyl fumarate, benzoic acid, trioxymethylene, cumarin, p-dichlorobenzene, ε-caprolactam, 1,4-cyclohexanediol, phthalide, lactide, triisopropyltrioxane and the like. They are used singly or in admixtures comprising two or more thereof.

In selecting the sublimable polar compounds, the properties of effective components to be incorporated should be taken into account. For example, when an effective component containing a hydroxyl group is used, it is generally preferred that a sublimable polar compound containing the same hydroxyl group is employed. Furthermore, it is desired that the amount of the sublimable polar compound added is determined according to the properties of sublimable hydrocarbons to be used in combination therewith. In the sublimable compositions of this invention, the amount of effective components contained therein can be increased with increasing proportion of the sublimable polar compound. However, the retention ratio of effective components markedly decreases when the sublimable polar compound forms a three-dimensional continuous phase, because it is possible for the effective components, of which many substances are relatively polar, to freely move through the carrier. In order to prevent the above phenomenon, it is desired that the composition ratio of a composition is determined so that the sublimable hydrocarbon be able to form a three-dimensional continuous phase in said composition.

When the melting point of a sublimable hydrocarbon is lower than that of a sublimable polar compound, the sublimable hydrocarbon forms a continuous phase in the composition. Thus the amount of the sublimable hydrocarbon added can be varied in a wide range. When the melting point of a sublimable hydrocarbon is higher than that of a sublimable polar compound, the amount of the sublimable polar compound added is not more than 20% by weight. If the amount is above 20% by weight, the continuous phase is reversed, that is, the sublimable polar compound forms a continuous phase in the composition. As a result, the retention ratio is extremely decreased.

The sublimation characteristics of a composition of this invention will vary according to the properties of each component of the composition: the term "sublimation characteristics" designates the phenomenon that the surface of a carrier does not become powder-coated.

Therefore, when the content and retention ratio of effective components such as a perfume and the like, and the sublimation characteristics of a carrier are collectively considered, the amount of the sublimable polar compound added will be determined as follows: in a TMN-dimethyl fumarate composition, the amount of dimethyl fumarate added is suitably 0.1 to 30 parts by weight: in a TMN-trioxymethylene composition, the amount of trioxymethylene is suitably 0.5 to 20 parts by weight; in a CD-dimethyl fumarate composition, the amount of dimethyl fumarate is suitably 0.1 to 60 parts by weight; and in a CD-benzoic acid composition, the amount of benzoic acid is suitably 0.1 to 30 parts by weight. Blending sublimable hydrocarbons and sublimable polar compounds in the ranges as described above provides the structure of a composition in which fine crystalline particles of the sublimable polar compound are dispersed in a uniform three-dimensional continuous phase of the sublimable hydrocarbon.

Since effective components such as a perfume and the like are gathered almost selectively in crystalline particles of the sublimable polar compound, the effective components do not come in contact with the sublimable hydrocarbon forming the continuous phase, resulting in no depression in the softening point. Therefore, the strength of a sublimable carrier formed of the present sublimable composition does not decrease.

The use of adamantane as a sublimable hydrocarbon in the present composition provides a composition having excellent characteristics. A composition containing adamantane is hereinafter referred to as Composition I. Adamantane is a non-toxic and odorless sublimable substance. As compared with other sublimable hydrocarbons, its shape retention after molding is good and the mechanical strength of a molding formed thereof is high. Furthermore, it can hold a relatively large amount of effective components in the spaces between its crystalline particles. It can thus be considered that adamantane has various properties as an especially excellent carrier in comparison with the above other sublimable hydrocarbons. However, when adamantane is used singly, its retention ability of effective components is still insufficient, and thus the effective components first volatilize and adamantane alone is left. Therefore, it is required for adamantane that it is used in combination with the above described sublimable polar compounds.

Composition I when molded has more excellent shape retention and mechanical strength as compared with compositions prepared from sublimable hydrocarbons other than adamantane. With regard to the composition ratio of adamantane and a sublimable polar compound, it is also desired as in the compositions prepared from other sublimable hydrocarbons and sublimable polar compounds that the proportion is determined so that no three-dimensional continuous phase of sublimable polar compounds used is formed and a three-dimensional phase of adamantane is formed. The concrete composition ratio of adamantane and a sublimable polar compound is necessary to be changed according to the properties of the sublimable polar compound employed. In general, it is desired that 80 to 10 parts by weight of adamantane is mixed with 20 to 90 parts by weight of sublimable polar compounds. But, when this composition is molded by melt molding, it is preferred that 50 to 10 parts by weight of adamantane is mixed with 50 to 90 parts by weight of sublimable polar compound.

The combined use of adamantane and other sublimable hydrocarbons provides quite excellent sublimable compositions. That is to say, in a composition comprising adamantane, other sublimable hydrocarbons and sublimable polar compounds (hereinafter referred to as Composition II), the softening point thereof doesn't be depressed markedly since the melting point of adamantane is high (268° C.). Thus the advantages of each component are sufficiently exhibited, resulting in the formation of an excellent sublimable carrier. Composition II contains adamantane as Composition I and thus its shape retention after molding is good and the mechanical strength of the molding is high. Moreover, since Composition II contains sublimable polar compounds, its ability to contain and retain effective components is excellent. These advantages are the same as those derived from Composition I. This Composition II, however, has an additional advantage since it contains sublimable hydrocarbons other than adamantane. That is to be capable of controlling easily the sublimation rate of the whole of the composition according to the kinds of effective components to be incorporated, or the use to which the composition is applied.

As sublimable hydrocarbons other than adamantane and sublimable polar compounds used in Composition II, the same as used in Composition I are used. The composition ratio of adamantane and other sublimable hydrocarbons is suitably determined according to the kinds of the sublimable hydrocarbons. When adamantane is mixed with TMN, 99 to 75 parts by weight of TMN is used per 1 to 25 parts by weight of adamantane. If the amount of TMN is below 75 parts by weight, the surface of the composition is coated with adamantane powder, the sublimation rate of adamantane being slower than that of TMN ($\frac{1}{5}$ of the sublimation speed of TMN), resulting in an undesirable deterioration of the composition properties.

Where adamantane and CD are employed, they can be mixed in any desired proportions. The reason for this is that since the sublimation rate of CD is slower than that of adamantane ($\frac{1}{2}$ of the sublimation rate of adamantane), although CD remains on the surface of the composition, it is in a three-dimensionally continuous uniform phase owing to the low melting point (60° C.) of CD and thus the surface of the composition does not become powder-coated. In general, it is preferred that 5 to 95 parts by weight of adamantane and 95 to 5 parts by weight of CD are blended.

Sublimable hydrocarbons other than adamantane principally act to control the sublimation rate of the whole of the composition. Therefore, in preparing a composition, one or more kinds of suitable sublimable hydrocarbons are selected according to the period during which it is necessary to retain the effective components such as a perfume and the like, and they are mixed in the above blending range. For example, where the composition is used as a spherical article having a weight of about 40 grams and a diameter of 40 millimeters, if the retention period of the effective components required is about one month, TMN is suitably employed, and if it is about six months (considered to be a period required when it is used as a sweet smell article for cars), CD is suitably employed.

The amount of a sublimable polar compound used in Composition II is preferably changed depending upon the properties of a sublimable hydrocarbon other than adamantane to be used in combination therewith. Where dimethyl fumarate is used as a sublimable polar compound, it is added in an amount of 0.1 to 15 parts by weight per 100 parts by weight of an adamantane-TMN composition (composed of 1 to 25% by weight of adamantane and 99 to 75% by weight of TMN), and to an adamantane-CD composition (composed of 5 to 95% by weight of adamantane and 95 to 5% by weight of CD), it is added in an amount of 0.1 to 40 parts by weight per 100 parts by weight of the adamantane-CD composition. Where benzoic acid is used, it is added in an amount of 0.1 to 10 parts by weight per 100 parts by weight of an adamantane-CD composition (composed of 5 to 95% by weight of adamantane and 95 to 5% by weight of CD). Where trioxymethylene is used, judging from a basis of sublimation characteristic, it would be capable of adding in an amount of 0.5 to 90 parts by weight per 100 parts by weight of an adamantane-TMN composition (composed of 1 to 25% by weight of adamantane and 99 to 75% by weight of TMN). But, in this case, if the retention effect of effective component is taken into consideration, the upper limit of an additional amount of it is reduced within one third. It is ideal that each sublimable polar compounds is added within the above range. If it is used outside the above range, either coating of powder on the surface or a lowering in strength is undesirably caused.

The above described compositions of the present invention; sublimable compositions comprising sublimable hydrocarbons and sublimable polar compounds, of which Composition II comprising adamantane, other sublimable hydrocarbons and sublimable polar compounds are especially preferred, has excellent various properties as sublimable carriers for retaining various effective components.

Effective components which can be incorporated in the above sublimable compositions, include a wide variety of compounds such as perfume, insecticides, insectirepellents, moth-proofing, attracting, and like agents, deodorants, rust preventives, mold-proofing agents, preservatives and the like. Suitable examples of the perfumes and deodorants include terpene based perfumes such as α-ionone, borneol, camphor, linalool, geraniol, citronellol, citronellal, citral, linalyl acetate, terpineol and the like; aromatic perfumes such as cumarin, nerolin, diphenyloxide, β-phenetylalcohol, acetophenone, benzylalcohol and the like; aliphatic perfumes such as alcohols, aldehydes, lactone and the like; animal perfumes such as musk, ambergris and the like; vegetable perfumes such as peppermint oil, lavender oil and the like; etc. Although it is most preferred that crystalline perfumes are used singly, liquid perfumes may be used. In general, they are used in admixtures therewith. The amount of the perfume added is usually sufficient to be not more than 10% by weight. Within this range, it is not necessary to change the composition ratio of the composition as described above.

As moth-proofing agents or insectirepellents, for example, for repelling mosquetos, phenetylalcohol, cineole, cinnamic alcohol and the like can be used. For the purpose of proofing clothes moths famous as harmful insects of wool, linalool, linalooloxide, l-menthol, thymol and the like are selected. In addition, cinnamic aldehyde, citronellol, diethyltoluamide, dibutyl phthalate and the like can be used as insectirepellents. The amount of moth-proofing agents or insectirepellents in the composition is 0.01 to 20% by weight. In adding these moth-proofing agents, if necessary, perfumes and other materials may be added.

As insecticides, 0,0-dimethyl-0-(2,2-dichlorovinyl) phosphate and the like can be used; as rust preventives, morphorine, dicyclohexylamine, diisopropylamine and the like can be used; as mold-proofing agents, ethyl pyrocarbonate, β-propiolactone and the like can be used. In addition, as preservatives, butyl p-hydroxybenzoate and the like can be used.

In the sublimable compositions of this invention, the above sublimable polar compounds contain and retain most of the effective components such as perfume and moth-proofing agents, and they decrease the distribution ratio of the effective components in adamantane and other sublimable hydrocarbons forming the three-dimensional continuous phase, thereby preventing a depression in softening point of the sublimable hydrocarbons. Therefore, no lowering in the mechanical strength of the composition is caused when the effective components are added to said composition. Since the sublimable polar compounds are discontinuously and numerously present in the non-polar adamantane or other sublimable hydrocarbons as fine crystalline particles and the effective components are adsorbed on or dissolved in the crystalline particle or slightly liquifying crystalline particle of the sublimable polar compound, the effective components volatilize concurrently with the sublimation of the sublimalbe composition although the volatility rate of the effective components and the sublimation rate of the sublimable composition are different from each other. Therefore, with regard to any kind of the effective components, the content of the effective component is materially constant during the sublimation of the carrier, and thus there is almost no change with a lapse of time.

Selection of components for a composition and determination of the amounts of the components to be added can be carried out in the order as shown below.

(1) To determine the desired sublimation rate of a carrier.

(2) To select one or more kinds of sublimable hydrocarbons (except for adamantane) taking into account said sublimation rate.

(3) To select effective component to be used.

(4) To select a sublimable polar compound adapted to the selected effective component.

(5) To determine the amounts of adamantane, the selected sublimable hydrocarbon and sublimable polar compound, and the effective component to be blended, according to the following equations.

$$V_A/V_{(B,X,Y)} \geqq G_A/G_{(B,X,Y)}$$

$$V_B/V_{(A,X,Y)} \geqq G_B/G_{(A,X,Y)}$$

$$V_X/V_{(A,B,Y)} \geqq G_X/G_{(A,B,Y)}$$

$$V_Y/V_{(A,B,X)} \geqq G_Y/G_{(A,B,X)}$$

V: Sublimation rate or volatility rate
G: Amount blended
A: Adamantane
B: Sublimable hydrocarbon (except for adamantane)
X: Sublimable polar compound
Y: Effective component When the melting point of B, X, or Y is below 100° C. and $V_B < V_A$, $V_X < V_A$, or $V_Y < V_A$, B, X, or Y may be incorporated into a composition in any desired proportions. Especially, when the retention effect of effective components is considered, the amount of sublimable polar compound possessing lower melting point than that of sublimable hydrocarbon should be limited within one fifth of total weight of a composition.

The sublimation rate and the like are calculated by putting temporary values in the above equations. By repeating this method of trial and error, the amounts of components satisfying the above equations can be determined. Those compositions obtained by blending the above ingredients in the above determined amounts are high in the effective component content, retention ratio and mechanical strength, and furthermore they are free from powder-coating thereon.

The effective components to be added to the compositions of this invention usually contain easily-oxidizable materials such as those compounds containing double-bonds, aldehydes, nitrogen-containing compounds, and the like. Therefore, antioxidants may be added together with the effective components in order to maintain the activities of the effective components for a long period of time.

The term "antioxidant" used in this invention designates organic compounds capable of preventing or controlling the action of oxygen to various autooxidative materials under the conditions of light and heat, etc., and it includes polymerization inhibitors and polymerization retarders. These antioxidants are divided into free radical chain stoppers, peroxide decomposers and metal deactivators according to the action mechanism thereof. They include quinones, aromatic amines, aldehydeamines, phenols and the like. The antioxidants used in this invention are desired to have a strong oxidation preventing ability, not to lose their volatility even though they themselves are oxidized, and to be little colored. In more detail, hydroquinone monomethyl ether, hydroquinone, resorcin, and the like are preferred. In addition, dibutyloxytoluene, butyloxyanisol, isoamyl gallate, phenylnapthylamine, BHT (2,6-di-tert-butyl-p-cresol), β-naphthol, sesamol, quercetin, and the like can be used.

While the amount of the antioxidant added is not limited, the antioxidant is usually added in an amount of 0.01 to 10% by weight of the effective component. Those compositions with these antioxidants incorporated therein are free from degeneration, polymerization and the like of the effective components during the use thereof. Thus, in these compositions, the effective components are all used to sufficiently exhibit their activities, and furthermore there is no residual of degenerated materials and polymerized materials.

A method of molding the sublimable compositions of this invention is not limited. For example, adamantane and/or other sublimable hydrocarbons and sublimable polar compounds are blended, heat-melted and uniformly mixed. If necessary, an effective component and an antioxidant are added thereto. The resulting mixture is cooled, solidified, divided and compression molded to form a molding having a desired form. The molding prepared by the above compression molding is uniform in the distribution of effective component, adamantane and the like, and its surface strength is insufficient. Furthermore, it is impossible to prevent the effective component from coming out from the surface during the compression.

On the other hand, when melt molding is employed, a molding can be obtained, in which the effective component is distributed in a low concentration on the outer portion of the molding and in a high concentration in the inner portion thereof. When adamantane is added, it is distributed in a high concentration on the surface of the molding and therefore the surface strength of the molding markedly increases. Moreover, releasability, dimensional accuracy and the like increase, and the surface of the molding is well finished. By this melt molding, the volatility of the volatile effective component is improved during the sublimation of the molding, resulting in an increase in the amount of the effective component retained in the molding.

The above described sublimable compositions prepared by combining the sublimable hydrocarbons and sublimable polar compounds generally markedly improve the volatility properties of the volatile liquid compounds. In these compositions, various mixtures of effective components having different boiling points which are added to achieve their own properties, are arranged so that they volatilize in proportion to a sublimable carrier on which they are supported. Therefore, since the carrier controls the volatility of the liquid materials, various liquid materials volatilize in the ratio thereof supported on the carrier. As a matter of course, therefore, when a molding being formed of a sublimable composition is sublimated, there would be no change in the composition ratio of the composition with a lapse of time.

However, when a sublimable molding is produced from said composition for practical use, even though the carrier comprised with sublimable hydrocarbon and a sublimable polar compound controls the volatility of liquid materials; effective components added thereto, the sublimation surface area of the molding often markedly changes during the sublimation. As a result, the volatility amount of the liquid materials markedly changes with a lapse of time.

Sublimable moldings whose sublimation area is not subject to a change with time, are those moldings of the disk type in which the ratio of diameter to thickness is great and cylinder type in which the sides are closed. On the other hand, as to moldings of general forms, their sublimation areas decrease during the sublimation thereof. Therefore, even though the volatility amount of the liquid material per unit sublimation area is constant, the volatility amount of the liquid material generally decreases and the predetermined or desired retention effect cannot be obtained.

Where a sublimable composition containing no sublimable polar compound: i.e., sublimable composition comprising adamantane or another sublimable hydrocarbon alone is employed as a sublimable carrier for a volatile liquid material, the volatility of each compound contained in the volatile liquid material and the sublimation of the sublimable carrier are unbalanced. The reason for this unbalance is considered that since the liquid freely moves through the inside of the solid sublimable carrier, a relatively volatile material is in a low concentration on the surface of the solid, thereby causing a gradient in concentration between the surface and the inner portion thereof. Therefore, the liquid material is apt to diffuse from the inner portion to the outside and the liquid material in the inner portion comes out to the surface. This phenomenon is illustrated in FIG. 17 referring to a model in relation to the sublimation of the carrier and the volatility of perfume.

For the purpose of controlling the diffusion of the liquid material, the sublimable composition of this invention has been developed which comprises sublimable hydrocarbons and sublimable polar materials. Thus it is possible to control the inner movement of the liquid material. FIG. 18-A illustrates the state that the liquid material added to the composition is retained by the sublimable polar compounds which can't move through the inner portion. As can be seen from these figures, the composition of this invention in which a sublimable polar compound is incorporated, when it is molded, has a high retention ratio of the effective component as compared with a composition in which no polar compound is incorporated.

However, it can be seen from Example 25 and Comparative Example 16 that if the composition of this invention is molded by compression molding, a relatively large amount of effective component oozes out. The difference in the arrangement of each components on the inside of molding between the molding produced by compression molding and melt molding is shown in FIG. 18-A and FIG. 18-B.

A sublimable carrier was prepared by freshly adding 4 parts by weight of dimethyl fumarate to a composition (Comparative Examples 18 and 19) comprising 20 parts by weight of adamantane and 80 parts by weight of TMN. To this sublimable carrier was added volatile linalool. The thus prepared composition was molded by melt molding to form a spherical molding. The volatility characteristics of the spherical molding are shown in Example 24. On the other hand, the same composition as used above was molded by compression molding to form a molding. With the molding so formed, a change with time of the linalool content was measured, and the results obtained are shown in Comparative Example 15.

The feature of the molding procedure of this invention is that in a molding obtained by melt molding from a composition comprising adamantane and/or other sublimable hydrocarbon, a sublimable polar compound and an effective component, the effective component (liquid material) added tends, as shown in FIG. 18-B, to accumulate in a high concentration in the inner portion thereof, and at the same time the sublimable polar compound itself is distributed in a higher concentration in the inner portion of the molding during the molding. Since the crystalline polar compound does not move through the inner portion during the sublimation, as the sublimation proceeds, the concentration of the effective component accompanied by crystalline polar compounds in the vicinity of the freshly formed surface increases. In Comparative Example 17, diethyl fumarate (liquid) was used in place of dimethyl fumarate used as a sublimable polar compound. From this Comparative Example, it can be seen that the above effect cannot be obtained by adding a liquid polar compound.

Where the melting point of a sublimable polar compound which is crystalline at ordinary temperature, is lower than that of a sublimable hydrocarbon which is used in combination with the sublimable polar compound, there is an extremely great difference in the retention property of a volatile liquid compound between those moldings produced by compression molding and melt molding. The volatility characteristics of a liquid compound, geraniol in a sublimable carrier in which TMN (m.p. 77) and trioxymethylene (m.p. 64° C.) are employed, is given in Example 23 and Comparative Example 14.

Although melt molding can be carried out by convention procedures, the molding temperature is preferably at least 10 to 20° C. higher than the temperature starting crystalization of a composition.

In moldings obtained by the melt molding of this invention, with regard to any kind of the effective components, a part of the effective component neither volatilizes excelusively fast nor remains. Therefore, the effect of the effective component is maintained at a constant level for a long period of time. Moreover, a molding obtained by the melt molding of this invention is sufficiently high in its mechanical strength and thus it can be quite effectively utilized as an aromatizing agent or perfume imparting agent, a moth-proofing agent, an insecticide, a deodorant, a rust preventive, a mold-proofing agent, a preservative, and the like. Moreover, when admantane is used in combination with other sublimable hydrocarbons, the time required for solidifying the molten compound is shortened and molding speed is increased, which are advantageous from the standpoint of production. Furthermore, adamantane is present in a high concentration on the surface of a molding and thus the surface strength of the molding is markedly increased. In addition, dimensional accuracy, releasability and the like are improved and the surface of the molding is thus well finished. At the same time, the shape retention ability after molding and the retention ability of effective components are increased.

Hereinafter, a sublimable multi-layer molding will be explained wherein a plurality of layers of the present compositions having different effective components contents are overlaid on each other so as to keep the volatility rate of the effective components at constant levels. This sublimable multi-layer molding is composed of sublimable hydrocarbon, sublimable polar compound and effective component, and thus this is characterized in that the effective component content in each layer is gradually increased toward the inner side or lower side from the surface layer. The sublimation rate of a molding contained in a container gradually decreases owing to diffusion control resulted from a barrier of container. Therefore, it is necessary to investigate multi-layer molding. The ratio of the effective component contained in each layer should be controlled so that the volatility ratio of the effective component is always kept constant during the sublimation of a molding. In general, since the volatility ratio of the effective component suddenly decreases after the starting of the sublimation, it is necessary to gradually increase the effective component content so as to prevent the sudden decrease. In order to keep the volatility ratio of the effective component at a constant level, for example, where one kind of effective component is employed, a sublimable carrier may be composed of a single sublimable hydrocarbon or a single sublimable polar compound. However, if two or more kinds of effective components are used, one kind of sublimable hydrocarbon and one or more kinds of sublimable polar compounds are used together for preparing a sublimable carrier. The reason for this is that where two or more kinds of effective components are used, the volatility ratio of the effective components are different from each other and as a result, the total volatility ratio does not become constant. Therefore, in order to remove the above problem, one or more kinds of sublimable polar compounds are dispersed in the molding to hold or retain therein the effective components so that the volatility ratio be constant in spite of the properties of each effective component.

The ratio in which the content of the effective component of each layer constituting a multi-layer molding is successively increased from the surface layer to the inner side or lower side, will vary depending upon the kind of a sublimable carrier, the kinds of the effective components, the thickness of each layer, the shape of the each layer, the sublimation conditions or the like. Therefore, it is not possible to determine the ratio unconditionally. In preferred embodiments, for example, if the thickness of a single layer is constant, in the case of a single sublimable carrier of TMN, para-dichlorobenzene and the like, the ratio of effective components in two layer adjacent to each other is 1:3 to 8; in case that sublimable hydrocarbons and sublimable polar compounds are combined, for example, TMN-dimethyl fumarate, adamantane-TMN-dimethyl fumarate systems are employed, the ratio is 1:1.2 to 4.

Although the shape and the lamination of the multi-layer molding of this invention are not especially limited, it is classified generally into the following two types. In the first type, as shown in FIG. 19, plate-like layers (disk layers, plate layers and the like) are laminated one upon another. This type of molding is preferably formed so that only the surface of the most upper layer is exposed to atmosphere and all of the other layers are shielded from air by wrapping or the like. In this kind of molding, if the effective component content is successively increased from the upper layer to the lower layer taking a variation between the sublimation rate of an initial layer and a present one into consideration, the upper layer is first consumed and then the lower layers are successively exposed to the air during the gradual sublimation of the molding. Thus it is possible to maintain the volatility ratio of the effective component at a constant level. In the second type, it is in the spherical form as shown in FIG. 20 wherein the outer layers are successively laminated on the inner layers such that the outer layer wraps the inner layer. In this case, if the content of the effective component is successively increased from the outer layer to the inner layer, it is possible to maintain the volatility ratio of the effective component at a constant level during the sublimation of the molding.

While the present multi-layer moldings prepared in the above described two kinds of forms are all preferably used, a molding of the type wherein the plate-like layers are overlaid one upon another as shown in FIG. 19 is economically advantageous from the standpoint of production. It is preferred that the number of the layers constituting the molding is increased, and it is ideal that the molding is composed of numberless layers and the effective component contents of the layers are successively changed. However, as the number of the layers increases, the production steps are more complicated, which is not practical. In the multi-layer molding of this invention, where two carriers comprising two layers of para-dichlorobenzene and two layers of TMN having the same thickness are separately prepared, it is preferred that the gradient in concentration between the upper layer and the lower layer is made greater in the para-dichlorobenzene based carrier as compared with that in the TMN based carrier so that the volatility ratio be maintained at a constant level, because the para-dichlorobenzene based carrier is more liable to release the effective component. In a TMN-dimethyl fumarate based carrier, since the dimethyl fumarate has the properties to volatilize two or more kinds of effective components in the same ratio and at the same time to retain the effective components in a certain point in the sublimable carrier, it is possible to obtain the substantially ideal volatility characteristics by decreasing the thickness of each layer and by laminating a number of layers to provide the gentle gradient in concentration.

The multi-layer molding of this invention can be formed by various procedures. For example, in producing a multi-layer molding of the type that plate-like layers are overlaid one upon another, a suitable sublimable carrier and an effective component are first molten and mixed, and the mixture is then introduced in a mold, cooled, and solidified to form a layer. Then, the effective component is added to the sublimable carrier in a smaller amount than that employed in the above layer. The resulting mixture is molten and mixed, and then it is poured into a mold in which the above formed layer has been placed, cooled, solidified and laminated on the above layer. In this way, this lamination is repeated to form an upper layer on a lower layer successively whereby a multi-layer molding is obtained, wherein the content of the effective component of each layer is increasing successively from an upper layer to a lower layer.

In the multi-layer molding of this invention, as described above, the volatility ratio of the effective component can be kept substantially constant during the use thereof, and as a result, the stable effect can be exhibited for a long period of time.

The following examples and comparative examples are given to make easier the understanding of this invention.

EXAMPLE 1

A mixture of 80 parts by weight of TMN and 4 parts by weight of dimethyl fumarate was prepared and uniformly mixed by heating. To 100 parts by weight of this mixture was added 2 parts by weight of geraniol. The resulting mixture was cooled rapidly, solidified and pulverized. 0.5 g of this powder was weighed out and compression molded at a pressure of 10 Kg/cm$^2$ to form a tablet of a diameter of 13.0 mm and a height of about 5 mm. Creep test was conducted at a load of 2 Kg. The results obtained are shown in FIG. 1.

COMPARATIVE EXAMPLE 1

The procedure of Example 1 was repeated wherein no dimethyl fumarate was used. The results obtained are shown in FIG. 1.

EXAMPLE 2

The procedure of Example 1 was repeated wherein no geraniol was used. The results obtained are shown in FIG. 1.

COMPARATIVE EXAMPLE 2

The procedure of Example 1 was repeated with the exception that TMN alone was used. The results obtained are shown in FIG. 1.

EXAMPLE 3

Figure 2:
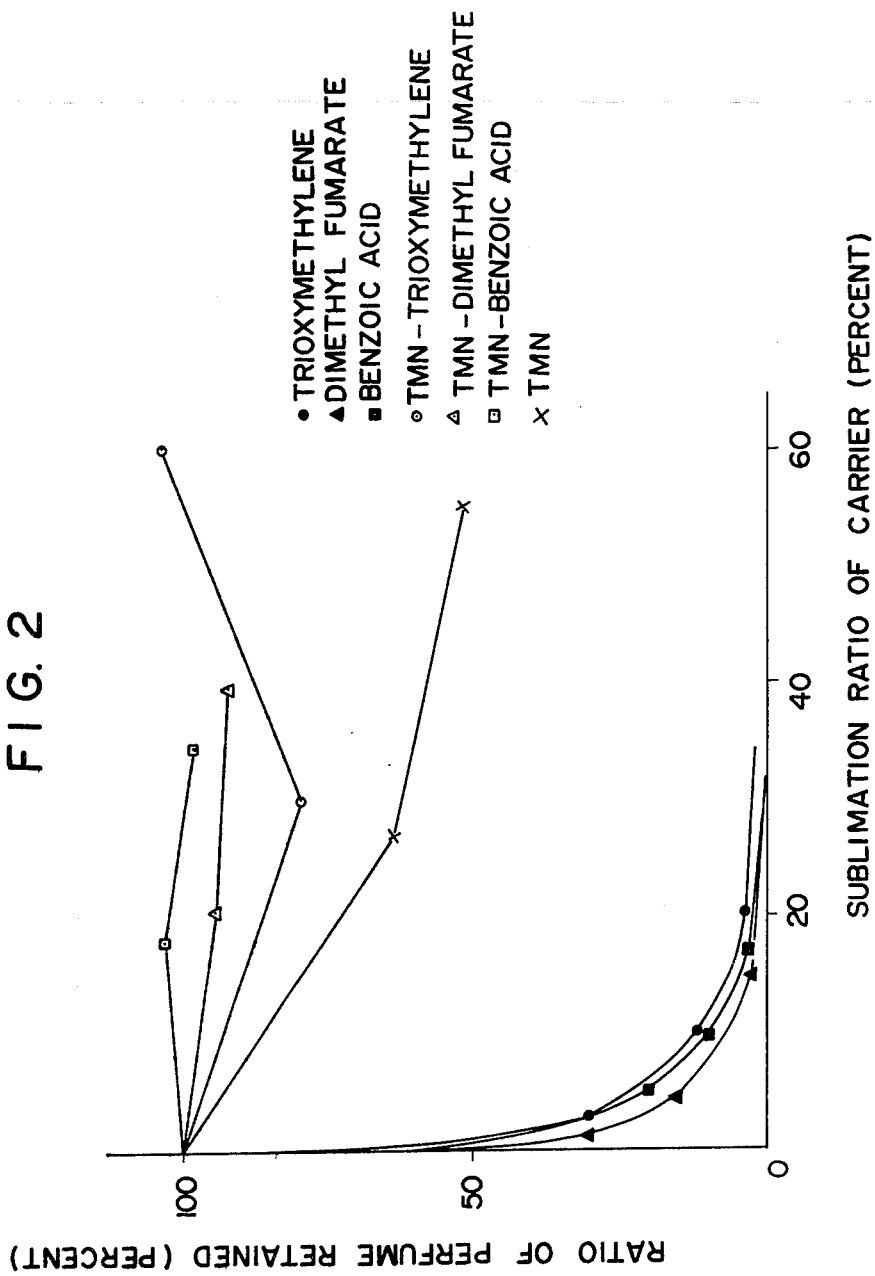

A mixture of 80 parts by weight of TMN and 20 parts by weight of a polar compound was prepared and melted by heating. To this molten mixture was added 2 parts by weight of geraniol. The resulting mixture was cooled rapidly and pulverized. 0.5 g of this powder was weighed out and molded into a tablet of a diameter of 13.0 mm and a height of about 5 mm at a molding pressure of 10 Kg/cm$^2$. This tablet was sublimated in a stream of air at room temperature and its retention ratio of perfume with a lapse of time was measured. The results obtained are shown in FIG. 2.

The initial perfume content after molding is shown in Table 1.

TABLE 1

| Composition | Initial Perfume Content (wt %) |
|---|---|
| TMN-Dimethyl Fumarate | 1.23 |
| TMN-Benzoic Acid | 1.32 |
| TMN-Trioxane | 0.95 |
| TMN | 0.80 |

EXAMPLE 4

The procedure of Example 3 was repeated with the exception that CD was used in place of TMN. The initial content after molding is shown in Table 2.

TABLE 2

| Composition | Initial Perfume Content (wt %) |
|---|---|
| CD-Dimethyl Fumarate | 0.77 |
| CD-Benzoic Acid | 0.65 |
| CD-Trioxane | 0.52 |
| CD | 0.16 |

EXAMPLE 5

Adamantane, TMN and dimethyl fumarate were mixed in a arbitrary proportion. This mixture was uniformly mixed by heating, and the resulting molten mixture was cooled, solidified, pulverized and compression molded to obtain a spherical sublimable molding of a diameter of 40 mm. This spherical molding was sublimated in a stream of air at room temperature, and the amount of powder (total amount of powder released from the surface of the spherical molding and powder attached to the spherical molding) after a lapse of 9 days was measured. The results obtained are shown in Table 3.

Figure 3:
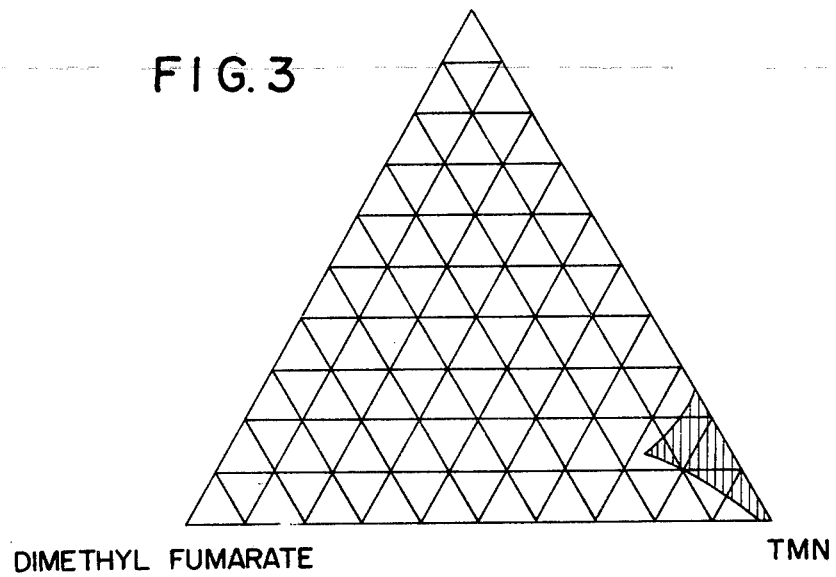
FIGS. 3, 4, 5 and 6 are triangular coordinates showing the ideal composition of three components.

The ideal composition not forming any powder on the surface of the composition, which was obtained by changing the proportions of the three components, is shown in FIG. 3.

TABLE 3

| Composition (parts by weight) Adamantane-TMN-Dimethyl Fumarate | | | Initial Weight (g) | Weight after 9 days (g) | Amount of Powder (g) |
|---|---|---|---|---|---|
| 10 | 80 | 10 | 36.8 | 19.9 | 0.68 |
| 20 | 80 | 5 | 37.5 | 19.8 | 0.00 |
| 20 | 80 | 10 | 37.4 | 22.0 | 0.00 |
| 0 | 80 | 20 | 36.8 | 20.9 | 2.36 |
| 30 | 70 | 5 | 37.0 | 21.2 | 1.53 |

EXAMPLE 6

Figure 4:
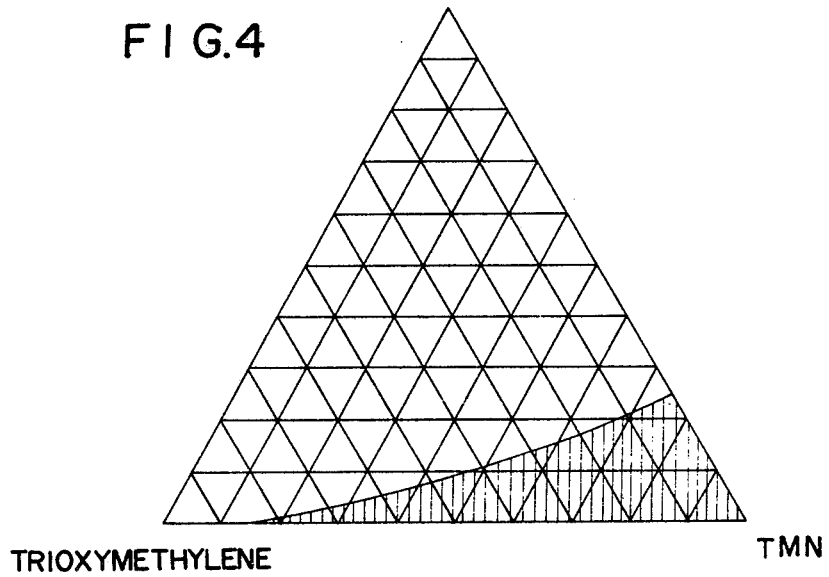

In the same manner as in Example 5, the ideal mixing range of an adamantane-TMN-trioxymethylene composition was determined. The results obtained are shown in FIG. 4.

EXAMPLE 7

Figure 5:
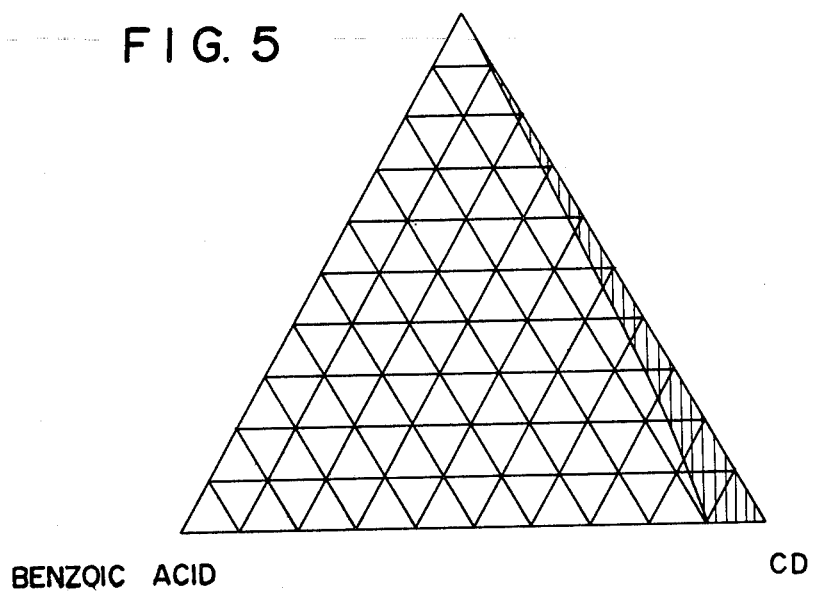

In the same manner as in Example 5, the ideal mixing range of an adamantane-CD-benzoic acid composition was determined. The results obtained are shown in FIG. 5.

EXAMPLE 8

Figure 6:
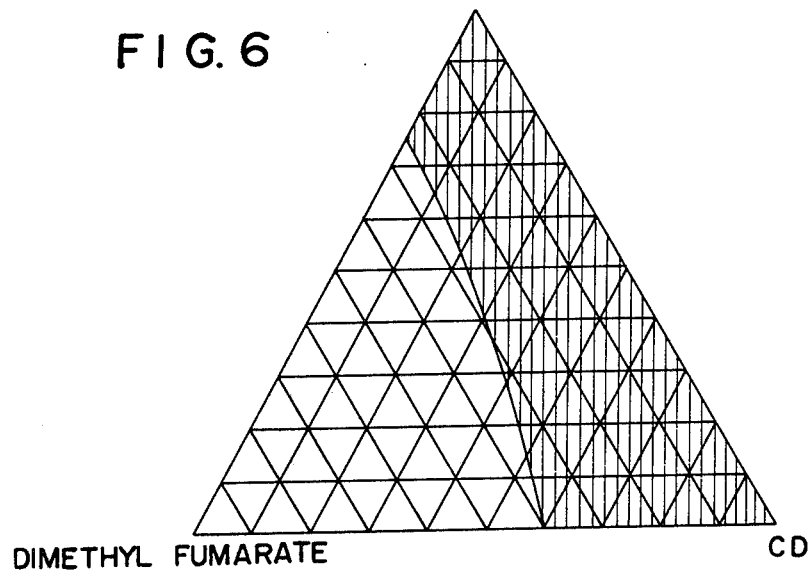

In the same manner as in Example 5, the ideal mixing range of an adamantane-CD-dimethyl fumarate composition was measured. The results obtained are shown in FIG. 6.

EXAMPLE 9

A mixture of 20 parts by weight of adamantane, 80 parts by weight of TMN, and 5 parts by weight of dimethyl fumarate was melted by heating and uniformly mixed. To this molten mixture was added 1 part by weight of perfume, and the resulting mixture was cooled rapidly, solidified and pulverized. 0.5 g of this powder was compression molded to form a tablet of a diameter of 12 mm and a height of about 5 mm. This tablet was sublimated in a stream of air at room temperature and the perfume content was measured when the weight of the tablet was ½ of the original one. The results obtained are shown in Table 4. This perfume content was indicated as a relative content when the initial content of the tablet after molding is set as 1.

EXAMPLE 10

The procedure of Example 9 was repeated with the exception that 5 parts by weight of dimethyl fumarate and 10 parts by weight of trioxymethylene were used as sublimable polar compounds. The results obtained are shown in Table 4.

COMPARATIVE EXAMPLES 3 and 4

The procedure of Example 9 was repeated with the exception that adamantane or TMN alone was used as a carrier. The results obtained are shown in Table 4.

TABLE 4

| Perfumes | Adamantane-TMN-Dimethyl Fumarate | Adamantane-TMN-Dimethyl Fumarate-Trioxymethylene | Adamantane | TMN |
|---|---|---|---|---|
| Terpene based perfumes | | | | |
| α-Ionone | 0.92 | — | — | — |
| Linalool | 0.85 | — | — | — |
| Geraniol | 0.98 | — | 0.73 | 0.58 |
| Citronellol | 0.92 | — | 0.69 | 0.54 |
| Citronellal | 0.83 | 0.94 | 0.58 | 0.48 |
| Citral | 0.64 | — | 0.52 | 0.46 |
| Linalyl Acetate | 0.69 | — | — | — |
| Aromatic perfumes | | | | |
| Diphenyloxide | 0.82 | — | 0.28 | 0.59 |
| β-Phenethyl Alcohol | 0.86 | — | 0.31 | 0.68 |
| Acetophenone | 0.79 | — | — | — |

EXAMPLE 11

Figure 7:
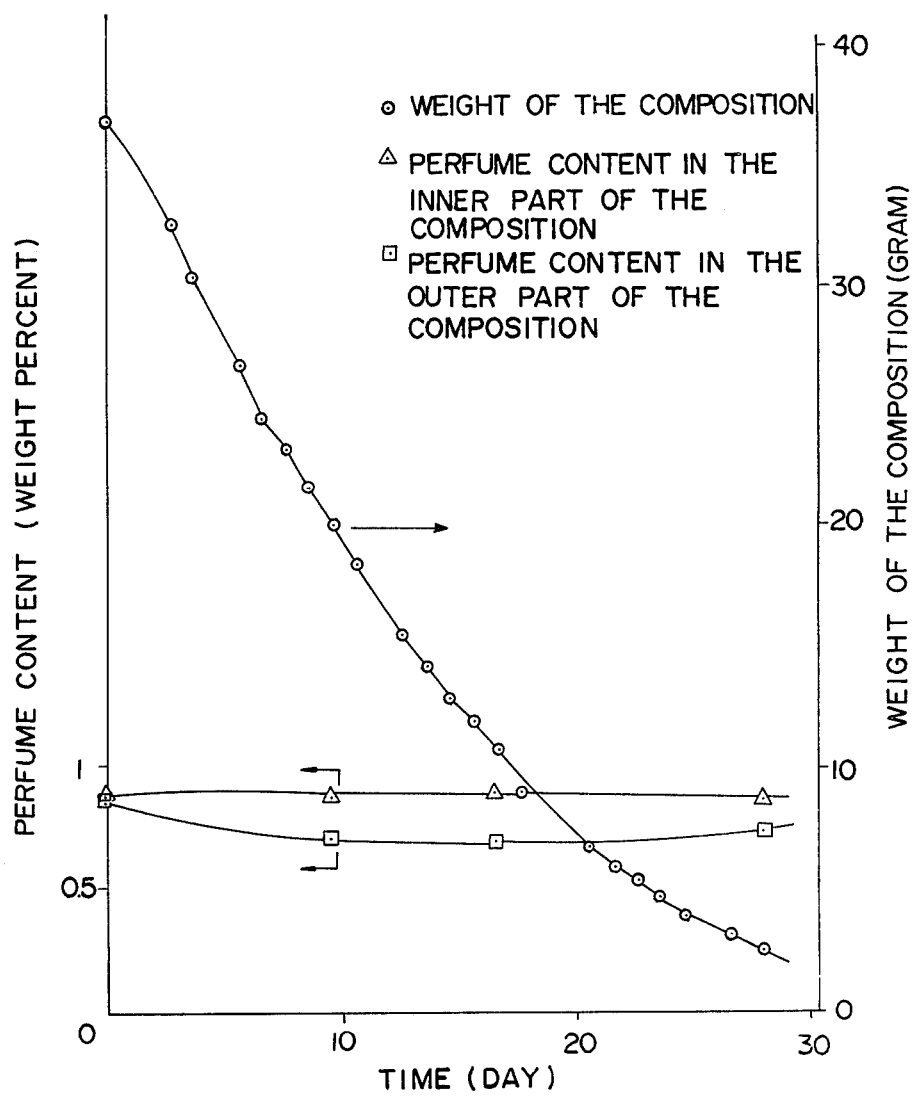
FIGS. 7 and 8 are graphs showing the sublimation characteristics and creep characteristics of the composition of this invention.

A mixture of 20 parts by weight of adamantane, 80 parts by weight of TMN and 5 parts by weight of dimethyl fumarate was melted by heating and uniformly mixed. To this molten mixture was added 1 part by weight of linalool. The resulting mixture was immediately cooled, solidified and pulverized. 37 g of this powder was compression molded to form a spherical molding having a diameter of 40 mm. This spherical molding was sublimated in a stream of air at room temperature, and the sublimation characteristics of the perfume and sublimable carrier were measured. The results obtained are shown in FIG. 7. From FIG. 7, it can be seen that the perfume content was constant even though the weight of the carrier decreased. With all of the perfumes used in Example 9, the same results were obtained.

EXAMPLE 12

Adamantane, CD and dimethyl fumarate were mixed in a arbitrary ratio, melted by heating and uniformly mixed. To this mixture was added 2 parts by weight of geraniol. The resulting mixture was immediately cooled, solidified and pulverized. 0.50 g of this powder was compression molded to form a tablet of a diameter of 13.0 mm and a height of about 5 mm. This tablet was sublimated in a stream of air at room temperature during 5 days and the volatility characteristics of geraniol were measured. The results obtained are shown in Table 5. The perfume content was indicated as a relative content when the initial perfume content of the tablet after the molding is set as 100%.

TABLE 5

| Composition (parts by weight) | | | Tablet after 5 days | |
| --- | --- | --- | --- | --- |
| Adamantane | CD | Dimethyl Fumarate | Weight (g) | Perfume Content (%) |
| 20 | 80 | 5 | 0.33 | 60 |
| 20 | 80 | 10 | 0.32 | 49 |
| 30 | 70 | 10 | 0.29 | 52 |
| 40 | 60 | 10 | 0.27 | 55 |
| 20 | 80 | 0 | 0.33 | 22 |

EXAMPLE 13

In Example 12, benzoic acid was used in place of dimethyl fumarate. The results obtained are shown in Table 6.

TABLE 6

| Composition (parts by weight) | | | Tablet after 5 days | |
| --- | --- | --- | --- | --- |
| Adamantane | CD | Benzoic Acid | Weight (g) | Perfume Content (%) |
| 20 | 80 | 5 | 0.38 | 67 |
| 20 | 80 | 10 | 0.32 | 42 |
| 30 | 70 | 10 | 0.32 | 86 |
| 40 | 60 | 10 | 0.29 | 43 |
| 20 | 80 | 0 | 0.33 | 22 |

EXAMPLE 14

A mixture of 20 parts by weight of adamantane, 80 parts by weight of TMN and 4 parts by weight of dimethyl fumarate was melted by heating and uniformly mixed. To this molten mixture was added 2 wt% of geraniol. The resulting mixture was immediately cooled and pulverized. 0.5 g of this powder was weighed out and compression molded at a pressure of 10 Kg/cm$^2$ to form a tablet of a diameter of 13.0 mm and a height of about 5 mm.

Figure 8:
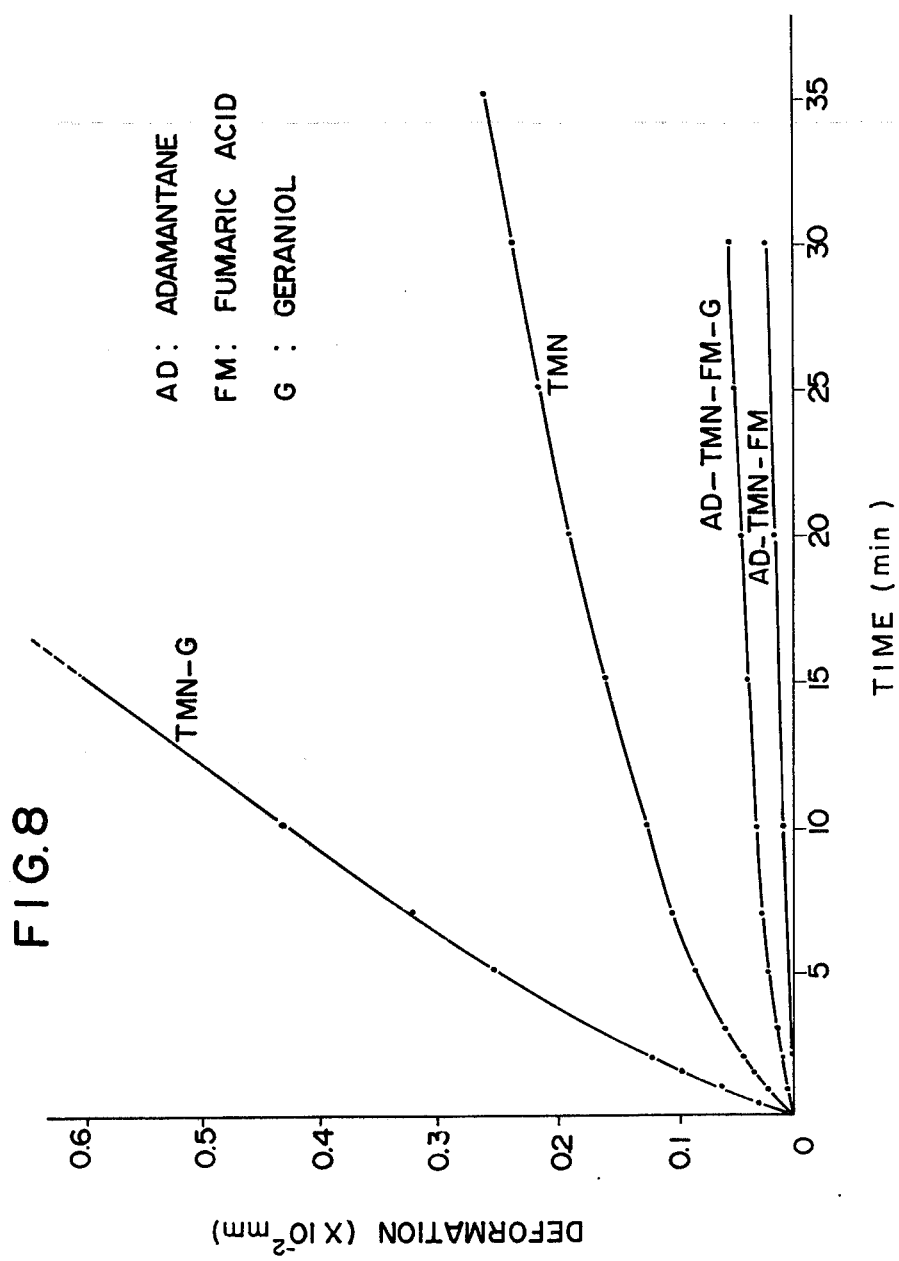

This tablet was subjected to creep test at a load of 2 Kg. The results obtained are shown in FIG. 8.

EXAMPLE 15

The procedure of Example 14 was repeated with the exception that no geraniol was added. The results obtained are shown in FIG. 8.

COMPARATIVE EXAMPLE 5

The procedure of Example 14 was repeated with the exception that 80 parts by weight of TMN alone was used as a carrier. The results obtained are shown in FIG. 8.

COMPARATIVE EXAMPLE 6

The procedure of Example 14 was repeated with the exception that TMN alone was used. The results obtained are shown in FIG. 8.

EXAMPLE 16

Figure 9:
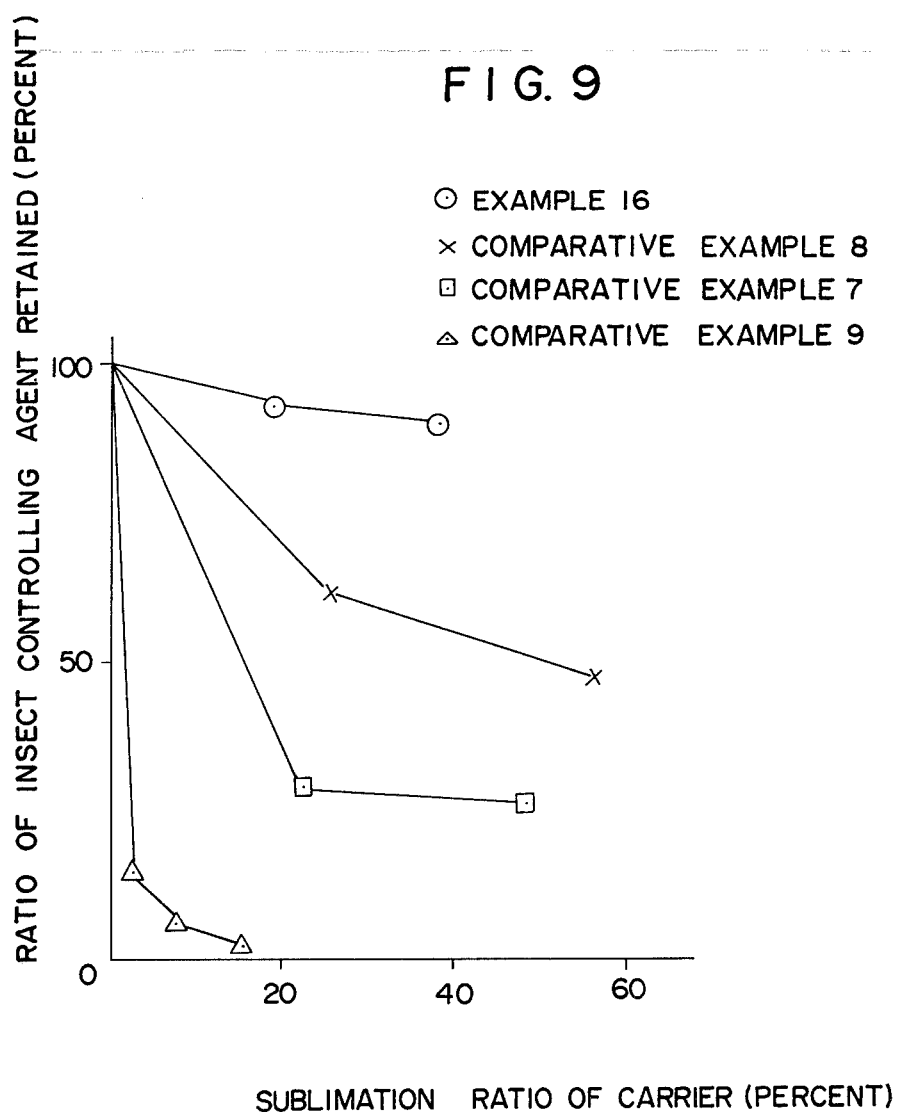
FIGS. 9 and 10 are graphs showing the relation between the retention ratio of a mothproofing agent and the sublimation ratio of a carrier.

A mixture of 20 parts by weight of adamantane, 80 parts by weight of TMN and 4 parts by weight of dimethyl fumarate was melted by heating. To this molten mixture was added 1 part by weight of l-menthol. The resulting mixture was cooled rapidly and pulverized. 0.5 g of this powder was molded at a molding pressure of 10 Kg/cm$^2$ to form a tablet of a diameter of 13.0 mm and a height of 5 mm. This tablet was sublimated in a stream of air at room temperature and a change with time in the retention ratio of the l-menthol was measured. The results obtained are shown in FIG. 9.

COMPARATIVE EXAMPLE 7

To 100 parts by weight of adamantane was added 1 part by weight of l-menthol. The resulting mixture was molded and subjected to sublimation test in the same manner as in Example 16. The results obtained are shown in FIG. 9.

COMPARATIVE EXAMPLE 8

To 100 parts by weight of TMN was added 1 part by weight of l-menthol. The resulting mixture was molded and subjected to sublimation test in the same manner as in Example 16. The results obtained are shown in FIG. 9.

COMPARATIVE EXAMPLE 9

To 100 parts by weight of dimethyl fumarate was added 1 part by weight of l-menthol. The resulting mixture was molded and subjected to sublimation test in the same manner as in Example 16. The results obtained are shown in FIG. 9.

EXAMPLE 17

Figure 10:
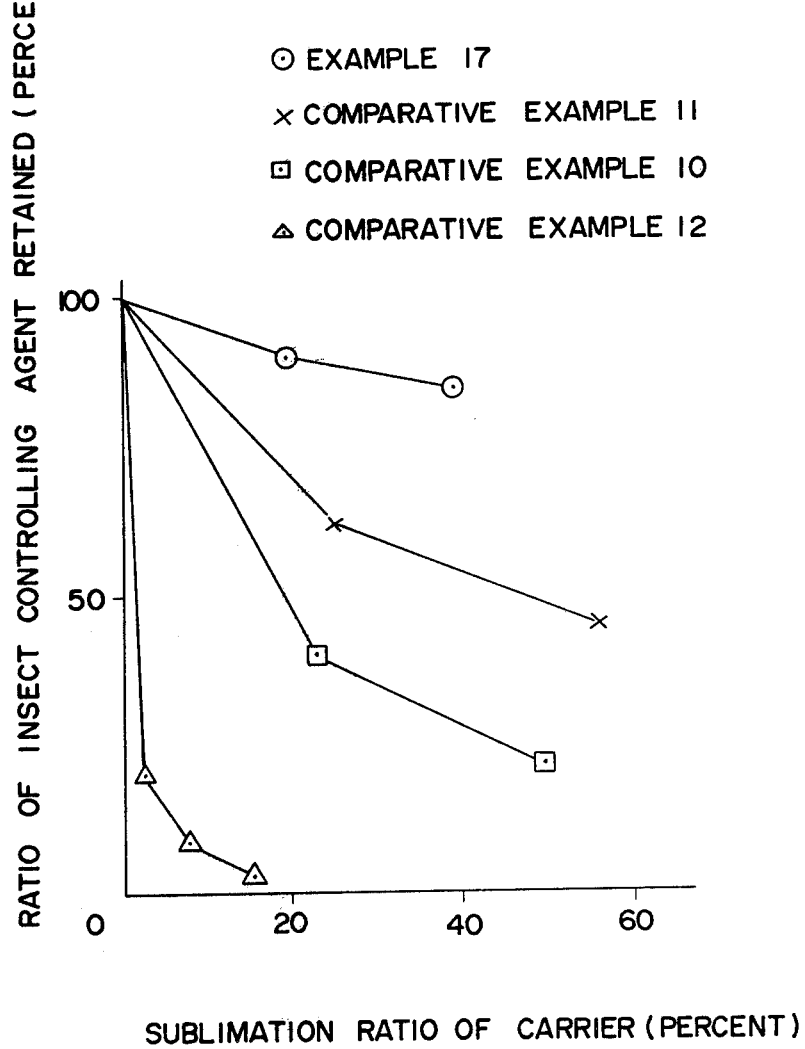

The procedure of Example 16 was repeated with the exception that β-phenetylalcohol was used in place of l-menthol. The results obtained are shown in FIG. 10.

COMPARATIVE EXAMPLE 10

To 100 parts by weight of adamantane was added 1 part by weight of β-phenetylalcohol. The resulting mixture was molded and subjected to sublimation test in the same manner as in Example 17. The results obtained are shown in FIG. 10.

COMPARATIVE EXAMPLE 11

To 100 parts by weight of TMN was added 1 part by weight of β-phenetylalcohol. The resulting mixture was molded and subjected to sublimation test in the same manner as in Example 17. The results obtained are shown in FIG. 10.

COMPARATIVE EXAMPLE 12

To 100 parts by weight of dimethyl fumarate was added 1 part by weight of β-phenetylalcohol. The resulting mixture was molded and subjected to sublimation test in the same manner as in Example 17. The results obtained are shown in FIG. 10.

EXAMPLE 18

A mixture of 20 parts by weight of adamantane, 80 parts by weight of TMN and 4 parts by weight of dimethyl fumarate was melted by heating and uniformly mixed. To this molten mixture was added 1 part by weight of a mothproofing agent. The resulting mixture was immediately cooled, solidified and pulverized.

This powder in the amount of 0.5 g was compression molded to form a tablet of a diameter of 13.0 mm and a height of about 5 mm. This tablet was sublimated in a stream of air at room temperature, and the retention ratio of the mothproofing agent was measured when the weight of the tablet was ½ of the original one. The results obtained are shown in Table 7. For comparison, the results obtained by using one of the compounds constituting the above carrier are shown in Table 7. The retention ratio of the mothproofing agent is indicated as a relative content when the initial content of the mothproofing agent in the tablet after the molding is set as 1.

TABLE 7

| Harmful Insect | Mothproofing Agent | Carrier | | | |
|---|---|---|---|---|---|
| | | Example 18 | Adamantane | TMN | Dimethyl Fumarate |
| Clothes Moth | Linalool | 0.85 | 0.52 | 0.53 | <0.01 |
| | Linalooloxide | 0.74 | 0.35 | 0.46 | <0.01 |
| | l-Menthol | 0.91 | 0.52 | 0.54 | <0.01 |
| | β-Phenetyl Alcohol | 0.86 | 0.31 | 0.68 | <0.01 |
| Mosquito | 1,8-Cineole | 0.70 | 0.28 | 0.42 | <0.01 |
| | Citronellol | 0.92 | 0.69 | 0.54 | <0.01 |

In case that thymol useful as a repellent for clothes mothes and cinnanic alcohol useful for mosquitos, which are not so easily volatile, are volatilized, their good sublimation can be attained by using CD in place of TMN as a sublimable hydrocarbon since sublimation rate of CD is relatively low.

EXAMPLE 19

In a stream of nitrogen, the following procedure was conducted: 20 parts by weight of adamantane, 80 parts by weight of TMN and 4 parts by weight of dimethyl fumarate were melted by heating and uniformly mixed, and 2 parts by weight of citral and a predetermined amount of antioxidant were added to the above mixture to form a solution, and this solution was charged to a mold for production of a spherical molding of a diameter of 40 mm whereby a spherical sublimable molding of a weight of about 30 g was obtained.

This molding was sublimated in a stream of air at room temperature and the volatility characteristics of the citral added were measured. Sublimation test was conducted. After a lapse of 21 days, the weight of the sample, the concentration of citral contained in the sample, and the weight of the residue which is insoluble in toluene were measured. The results obtained are shown in Table 8. Also, the results obtained without using antioxidant are shown in Table 8.

Figure 11:
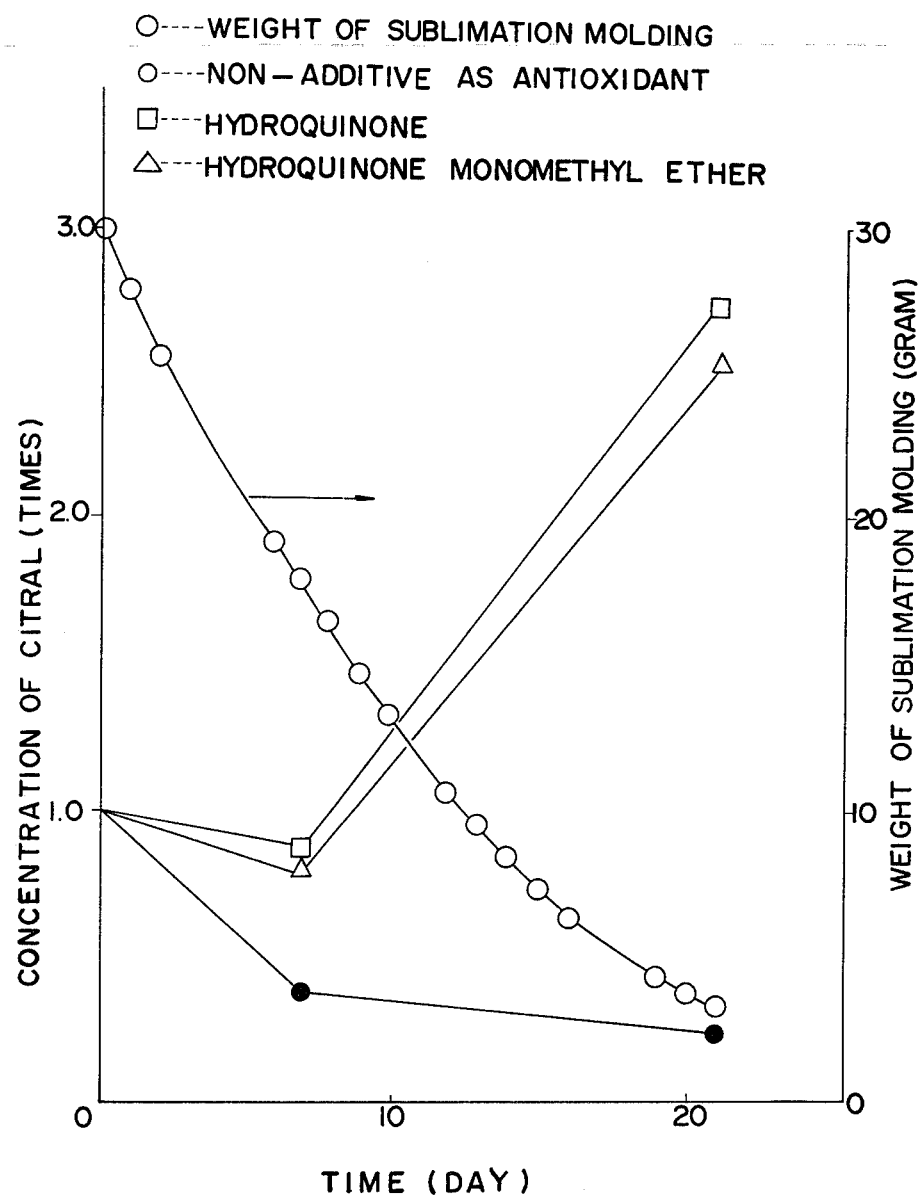
FIG. 11 is a graph showing the retention effect of perfume by addition of an antioxidant.

The retention effect of citral in the case that an antioxidant was added in an amount of 0.1 part by weight was measured, and the results shown in FIG. 11 were obtained. In this case, a change with time in the concentration of citral contained in the sublimable carrier was indicated as magnification to the initial concentration (1.9%).

TABLE 8

| Antioxidant | Amount (parts by weight) | Weight of Sample (g) | Concentration of Citral (%) | Weight of Toluene-insoluble Residue (mg) |
|---|---|---|---|---|
| Hydroquinone | 0.1 | 3.3 | 5.2 | 43 |
| | 0.01 | 3.7 | 3.8 | 53 |
| Hydroquinone Monomethyl Ether | 0.1 | 3.5 | 4.8 | 50 |
| | 0.01 | 3.3 | 3.4 | 65 |
| Resorcine | 0.1 | 3.1 | 6.6 | 25 |
| | 0.01 | 3.4 | 4.7 | 72 |
| No addition | — | 4.1 | 0.4 | 194 |

EXAMPLE 20

A mixture of 20 parts by weight of adamantane and 80 parts by weight of p-dichlorobenzene was melted by heating and uniformly mixed to form a solution. This solution was charged to a mold for production of a spherical molding of a diameter of 40 mm to produce a spherical sublimable molding of a weight of 30 g.

The thus obtained spherical molding was divided into two parts along the equator thereof. From each of the outer surface at the equator and the core portion of the molding was taken 0.5 g of an analysis sample. With these samples, the concentration distribution of adamantane was measured. The results obtained are shown in Table 9. In this Table 9, the average values indicate those which were obtained by dissolving the whole of the spherical molding in toluene and then measuring the adamantane concentration.

COMPARATIVE EXAMPLE 13

A mixture of 20 parts by weight of adamantane and 80 parts by weight of p-dichlorobenzene was melted by heating and uniformly mixed. Then this mixture was immediately cooled, solidified and pulverized.

This powder was compression molded at a molding pressure of 20 Kg/cm² to form a spherical molding of a diameter of 40 mm. In the same manner as used in Example 20, the concentration distribution of adamantane was measured. The results obtained are shown in Table 9.

TABLE 9

| | Molten Molding | Compression Molding |
|---|---|---|
| Outer Surface | 22% | 20% |
| Core Portion | 16% | 20% |
| Average Value | 20% | 20% |

EXAMPLE 21

A mixture of 20 parts by weight of adamantane and 80 parts by weight of p-dichlorobenzene was melted by heating and uniformly mixed. To this mixture was added 1 part by weight of linalool to form a solution. The thus obtained solution was charged to a mold for production of a spherical molding of a diameter of 40 mm to form a sublimable spherical molding of a weight of about 40 g.

From the thus obtained spherical molding were taken out samples in the same manner as in Example 20, and the concentration distributions of adamantane and linalool were measured. The results obtained are shown in Table 10. In indicating the concentration distribution, the higher concentration of linalool in either the outer surface or the core portion is indicated as 100, and the concentration of the other is given as a relative value.

EXAMPLE 22

A mixture of 10 parts by weight of adamantane and 90 parts by weight of dimethyl fumarate was melted by heating and uniformly mixed. To this mixture was added 2 parts by weight of linalool to form a solution. This solution was processed in the same manner as in Example 22. The results obtained are shown in Table 10.

TABLE 10

|  | Example 21 | Example 22 |
| --- | --- | --- |
| Distribution of Adamantane |  |  |
| Outer Surface | 100 | 100 |
| Core Portion | 73 | 71 |
| Distribution of Linalool |  |  |
| Outer Surface | 19 | 43 |
| Core Portion | 100 | 100 |

EXAMPLE 23

A mixture of 80 parts by weight of TMN and 20 parts by weight of trioxymethylene was melted by heating and uniformly mixed. To this mixture was added 1.6 parts by weight of geraniol to form a solution. The solution so obtained was charged to a mold for production of a spherical molding of a diameter of 40 mm to give a spherical sublimable molding of a weight of about 30 g.

Figure 12:
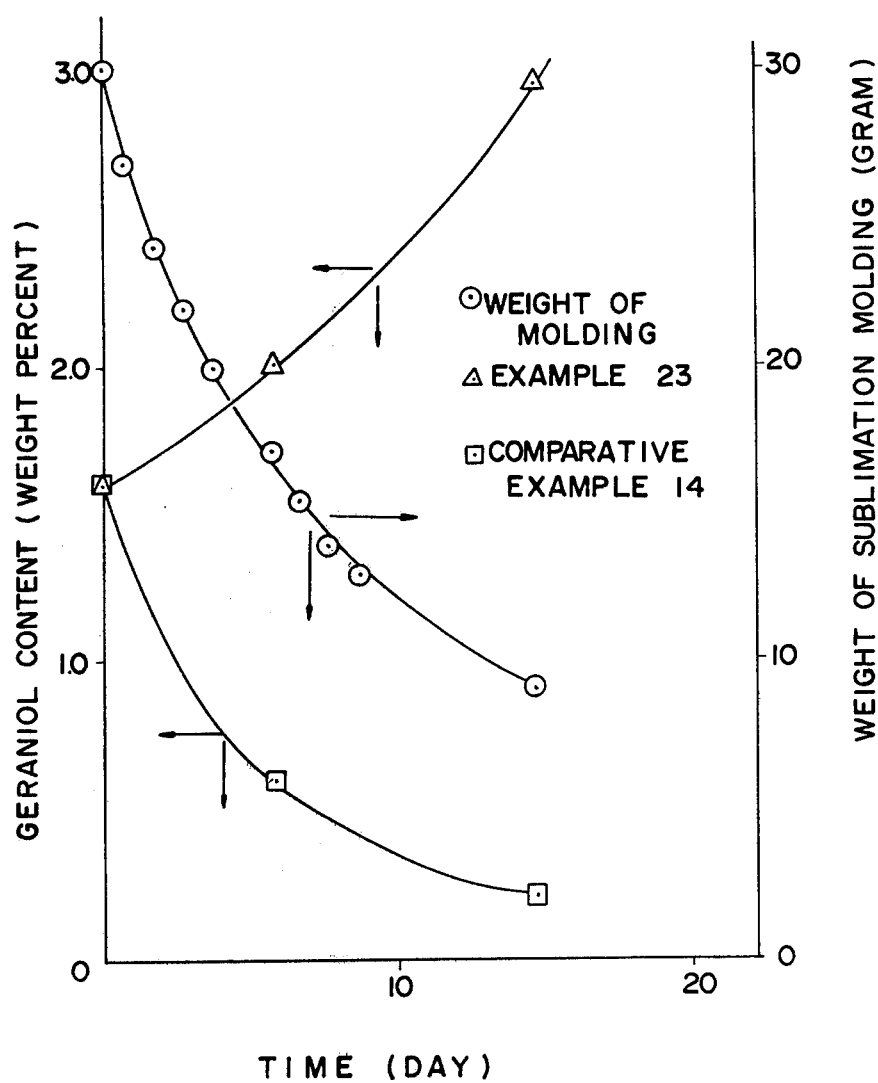
FIGS. 12 through 16 are graphs showing changes with time in volatility characteristics of a volatile additive from a molding and in weight of the molding.

The thus obtained spherical molding was sublimated in a stream of air at room temperature, and the volatility characteristics of the volatile liquid compound added were measured. The results obtained are shown in FIG. 12.

As can be seen from the Figure, the retention ability of this molding is quite excellent as compared with a molding produced by compression molding (Comparative Example 14).

COMPARATIVE EXAMPLE 14

In the same manner as in Example 23, a solution consisting of TMN, trioxymethylene and geraniol was obtained. This solution was immediately cooled, solidified and pulverized. This powder was compression molded at a molding pressure of 20 Kg/cm$^2$ to form a spherical molding of a diameter of 40 mm and a weight of about 30 g.

The thus obtained spherical molding was sublimated in the same manner as in Example 23, and the sublimation characteristics of the volatile liquid compound were measured. The results obtained are shown in FIG. 12. The concentration of geraniol contained in the spherical molding before the sublimation thereof was 1.6% by weight.

EXAMPLE 24

A mixture of 20 parts by weight of adamantane, 80 parts by weight of TMN and 4 parts by weight of dimethyl fumarate was melted by heating and uniformly mixed. To this mixture was added 1 part by weight of linalool to form a solution. This solution was charged to a mold for production of a spherical molding of a diameter of 40 mm to form a spherical sublimable molding of a weight of about 30 g.

Figure 13:
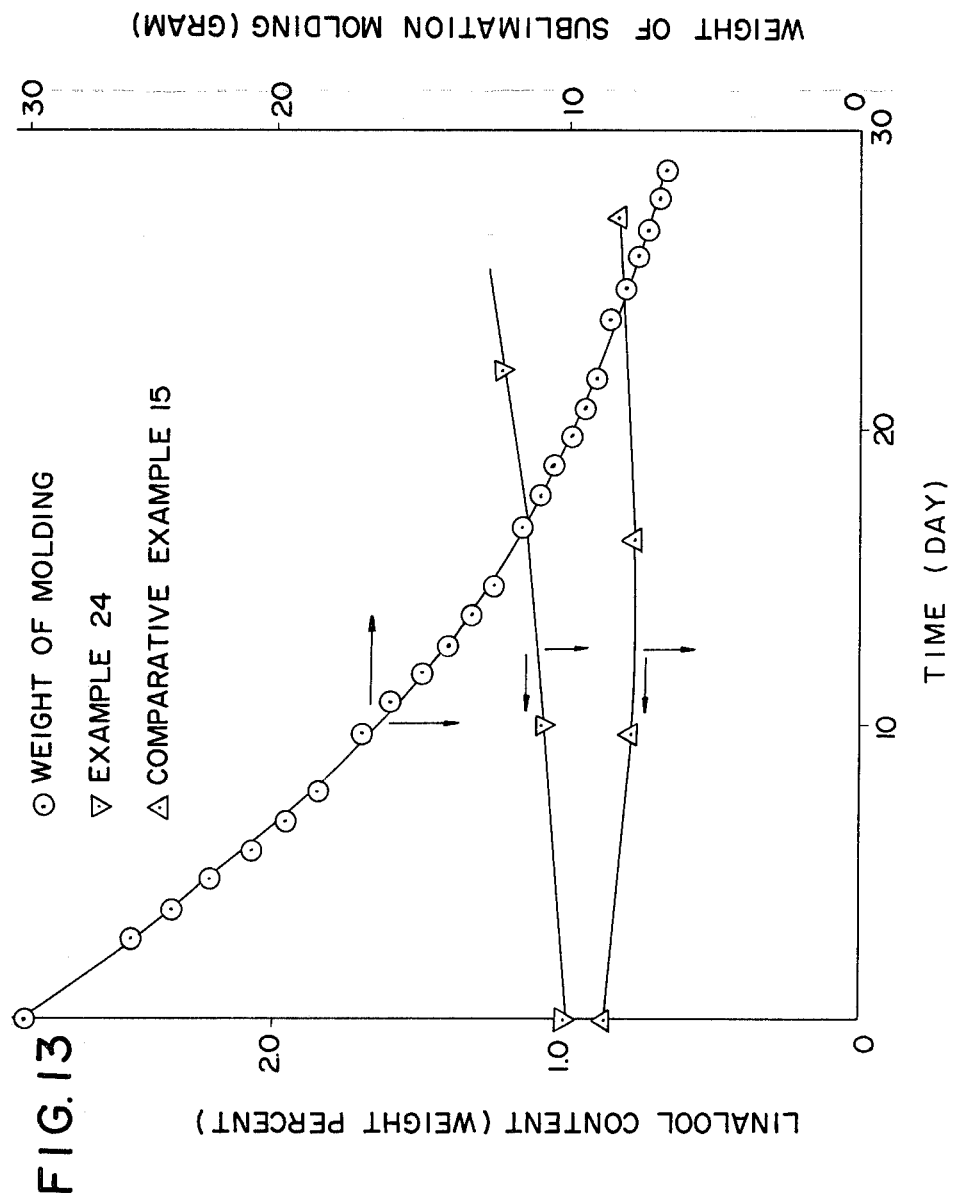

The thus obtained spherical molding was sublimated in the same manner as in Example 23, and the volatility characteristics of the volatile liquid compound added were measured. The results obtained are shown in FIG. 13. As apparent from the figure, during the course that the weight of the carrier was decreasing, the content of the liquid compound in unsublimated carrier was somewhat concentrated and increased. This indicates that the volatility of the inherently volatile liquid compound was controlled, and thus this molding is epoch-making.

EXAMPLE 25

Figure 14:
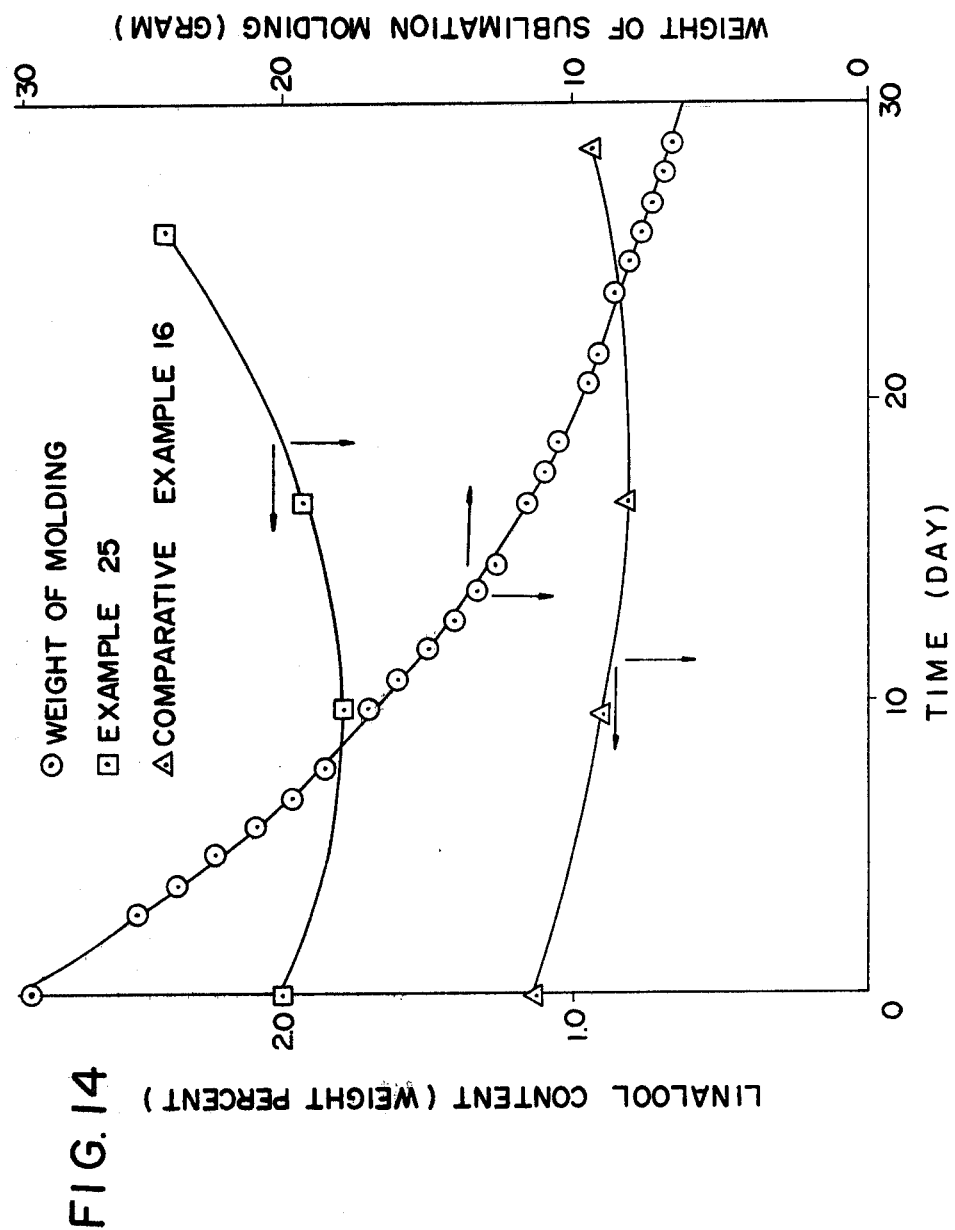

The procedure of Example 23 was repeated with the exception that 2 parts by weight of linalool was used in place of 1.6 parts by weight of geraniol. The results obtained are shown in FIG. 14.

COMPARATIVE EXAMPLE 15

A mixture of 20 parts by weight of adamantane, 80 parts by weight of TMN and 4 parts by weight of dimethyl fumarate was melted by heating and uniformly mixed. To this mixture was added 1 part by weight of linalool. The resulting mixture was immediately cooled, solidified and pulverized. This powder was molded into a spherical molding of a diameter of 40 mm and a weight of about 30 g by the same procedure as in Comparative Example 14.

With the thus obtained spherical molding, the volatility characteristics of the liquid compound were measured by the same procedure as used in Example 23. The results obtained are shown in FIG. 13.

COMPARATIVE EXAMPLE 16

The procedure of Comparative Example 15 was repeated with exception that the weight of linalool was changed to 2 parts by weight. The results obtained are shown in FIG. 14.

EXAMPLE 26

A mixture of 20 parts by weight of adamantane, 80 parts by weight of TMN and 4 parts by weight of dimethyl fumarate was melted by heating and uniformly mixed. To this mixture was added 2 parts by weight of a volatile liquid compound. The resulting solution was charged to a mold for production of a spherical molding of a diameter of 40 mm to form a spherical sublimable molding of a weight of about 30 g.

The thus obtained spherical molding was divided into two parts along the equator thereof. From each of the outer surface at the equator, the intermediate portion and the core portion of the molding was taken 0.5 g of an analysis sample, and the concentration distribution of the liquid compound contained in each portion was measured. The results obtained are shown in Table 11. The concentration distribution of the liquid compound in each portion is indicated with the concentration thereof in the outer surface as a base.

TABLE 11

| | Volatile Liquid Compound | | |
|---|---|---|---|
| | Linalool | Citronellal | Linalyl Acetate |
| Outer Surface | 1.0 | 1.0 | 1.0 |
| Intermediate Portion | 1.4 | 1.5 | 1.3 |
| Core Portion | 2.3 | 2.3 | 1.9 |

COMPARATIVE EXAMPLE 17

Figure 15:
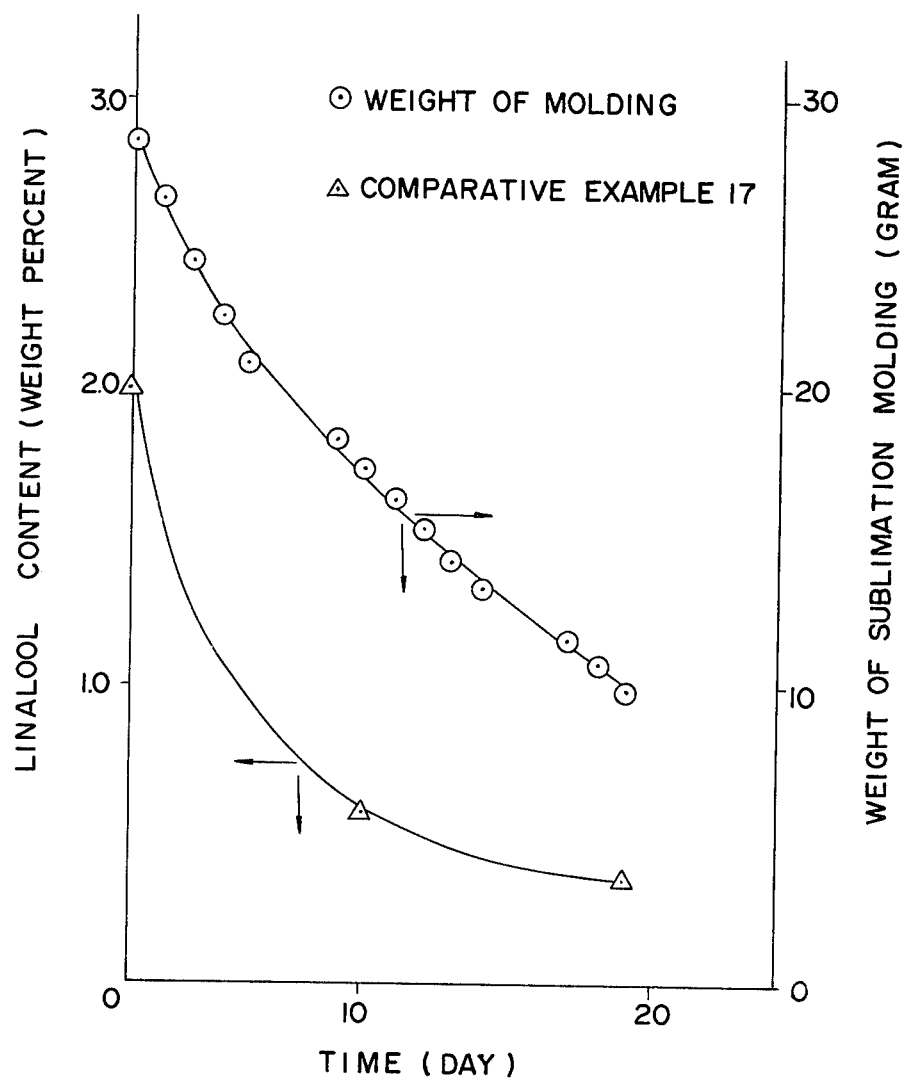

The procedure of Example 25 was repeated with the exception that diethyl fumarate, volatile polar compound was used in place of dimethyl fumarate. The results obtained are shown in FIG. 15.

COMPARATIVE EXAMPLE 18

A mixture of 20 parts by weight of adamantane, and 80 parts by weight of TMN was melted by heating and uniformly mixed. To this mixture was added 1 part by weight of linalool to prepare a solution. This solution was charged to a mold for production of a spherical molding of a diameter of 40 mm to form a spherical sublimable molding.

Figure 16:
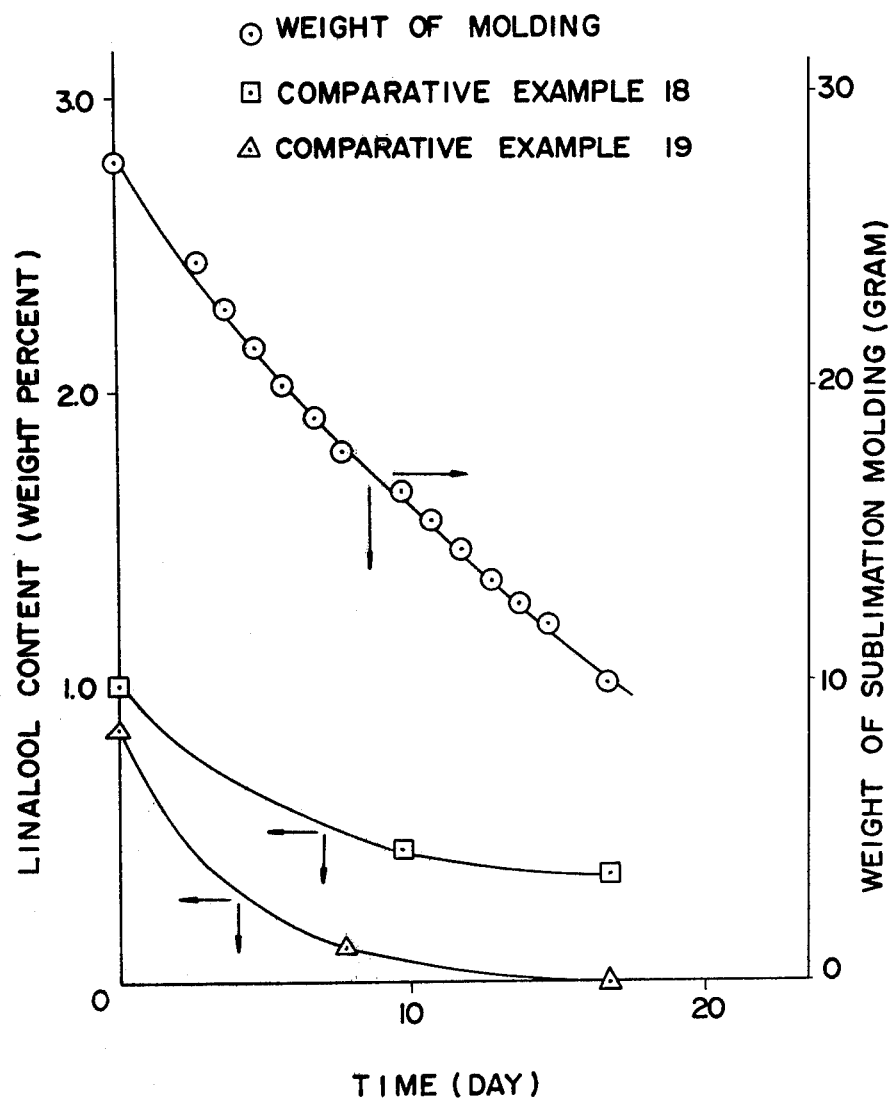

With the thus obtained spherical molding, the volatility characteristics of the liquid compound were measured in the same manner as in Example 23. The results obtained are shown in FIG. 16.

COMPARATIVE EXAMPLE 19

A mixture of 20 parts of adamantane and 80 parts by weight of TMN was melted by heating and uniformly mixed. To this mixture was added 1 parts by weight of linalool. The resulting mixture was immediately cooled, solidified and pulverized. This powder was compression molded to form a molding of a diameter of 40 mm.

The thus obtained molding was processed in the same manner as in Comparative Example 18. The results obtained are shown in FIG. 16.

EXAMPLE 27

A mixture of 20 parts of adamantane, 80 parts by weight of TMN and 4 parts by weight of dimethyl fumarate was melted by heating and uniformly mixed. To this mixture was added 3.5 parts by weight of linalool. The resulting mixture was cooled rapidly and pulverized. 0.5 g of this powder was compression molded to form a tablet of a diameter of 13.0 mm and a height of about 5 mm. In this molding, the molding pressure was set at 5, 10, 20 or 30 Kg/cm$^2$G, and the concentration of linalool in the tablet was measured. The amount of linalool added was changed to 10 parts by weight and the effect of molding pressure on the linalool concentration was measured. The results obtained are shown in Table 12.

TABLE 12

Effect of Compression Molding Pressure on Amount of Liquid Compound carried

| Molding Pressure | Amount of Linalool added | |
|---|---|---|
| (Kg/cm$^2$) | 3.5 parts by weight | 10 parts by weight |
| 5 | 1.4 | 1.6 |
| 10 | 1.3 | 1.5 |
| 20 | 1.4 | 1.6 |
| 30 | 1.4 | 1.5 |

EXAMPLE 28

A mixture of 100 parts by weight of TMN, 4 parts by weight of dimethyl fumarate and 8 parts by weight of linalool was melted by heating, charged to a mold and solidified by cooling to form a disk-like molding of a diameter of 42 mm and a height of 8.2 mm.

A mixture of 100 parts by weight of TMN, 4 parts by weight of dimethyl fumarate and 2 parts by weight of linalool was melted by heating. This molten solution was placed on the surface of the above prepared molding, and solidified by cooling to provide a laminated disk-like molding of a diameter of 42 mm, a height of 16.4 mm and a weight of 22.6 g.

This laminated molding was sublimated in a stream of air at room temperature. The upper surface (that is, the surface where the linalool concentration is low) was first sublimated. A change in weight of the molding and a change with time in the linalool content were measured. From this linalool content, a change with time in the volatility ratio of linalool per day was measured. The results obtained are shown in FIG. 21.

EXAMPLE 29

A laminated molding comprising a lower layer composed of 20 parts by weight of adamantane, 80 parts by weight of TMN, 4 parts by weight of dimethyl fumarate and 4 parts by weight of linalool, and an upper layer composed of 20 parts by weight of adamantane, 80 parts by weight of TMN, 4 parts by weight of dimethyl fumarate and 1 part by weight of linalool was produced by the same procedure as described in Example 28.

Figure 22:
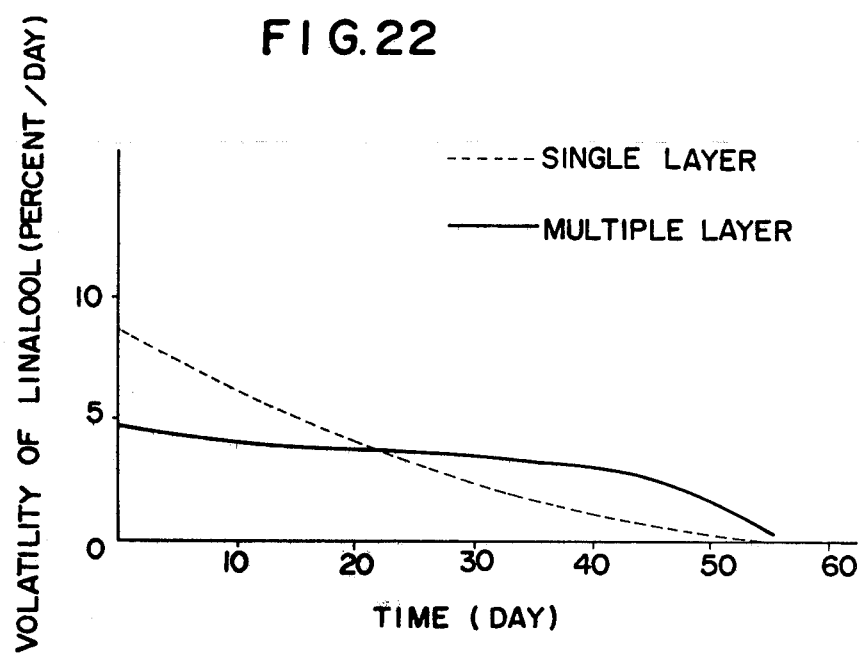
FIG. 22 shows a change with time in the volatility ratio of linallol of Example 29 and Comparative Example 20.

With the thus obtained molding, a change with time in volatility ratio was measured, and the results obtained are shown in FIG. 22. As can be seen from the figure, addition of adamantane can lengthen the life of the carrier as compared with the TMN-dimethyl fumarate based carrier.

COMPARATIVE EXAMPLE 20

A mixture of 20 parts by weight of adamantane, 80 parts by weight of TMN, 4 parts by weight of dimethyl fumarate and 2.5 parts by weight of linalool was melted by heating. This molten mixture was charged to a mold and solidified by cooling to form a disk-like mono-layer molding of a diameter of 42 mm, a height of 16.4 mm and a weight of 32.5 g. This mono-layer molding was sublimated in a stream of air at the room temperature. The upper surface was first sublimated. A change with time in the volatility ratio is shown in FIG. 22.

EXAMPLE 30

A laminated molding comprising a lower layer composed of 20 parts by weight of adamantane, 80 parts by weight of TMN, 4 parts by weight of dimethyl fumarate, 4 parts by weight of linalool and 4 parts by weight of linalyl acetate, and an upper layer composed of 20 parts by weight of adamantane, 80 parts by weight of TMN, 4 parts by weight of dimethyl fumarate, 1 part by weight of linalool and 1 part by weight of linalyl acetate was produced by the same procedure as used in Example 28.

Figure 23:
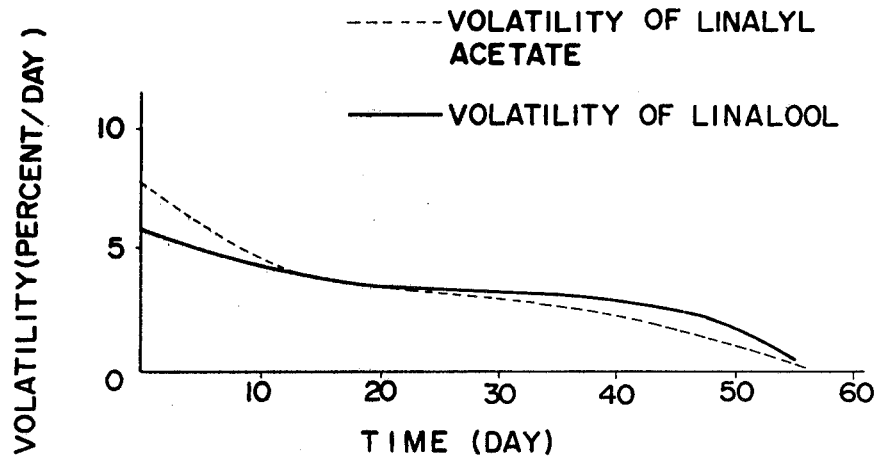
FIG. 23 shows a change with time in the volatility ratio of perfume of Example 30.

With the thus obtained laminated molding, a change with time in the volatility ratio was measured, and the results obtained are shown in FIG. 23.

EXAMPLE 31

A mixture of 20 parts by weight of adamantane, 80 parts by weight of TMN, and 1 part by weight of ε-caprolactam was melted by heating and uniformly mixed. To this molten mixture was added 2 parts by weight of dicyclohexylamine as rust preventive and the resulting mixture was poured into a tray, which is an open container having a diameter of 90 mm and a height of 20 mm, cooled and solidified. The weight of the disk obtained was 30 g.

This disk was sublimated in a stream of air at room temperature during 16 days and the concentration of dicyclohexylamine was measured. The result obtained is shown in Table 13. The retention ratio of dicyclohexylamine is indicated as the value that the content of the disk after sublimation was divided by the initial one.

As comparative example, above procedure without adding $\epsilon$-caprolactam was repeated and its result is shown in Table 13.

TABLE 13

| | Carrier | |
|---|---|---|
| | Adamantane-TMN-$\epsilon$-caprolactam | Adamantane-TMN |
| Retention ratio | 1.02 | 0.23 |

From Table 13, it was understood that dicyclohexylamine possessing rust preventive ability volatilized in proportion to a carrier which was composed of sublimable hydrocarbon and sublimable polar compound.

What is claimed is:

1. A sublimable composition comprising 1 to 25 parts by weight of adamantane, 99 to 75 parts by weight of endo-trimethylenenorbornane and 0.1 to 15 parts by weight of dimethyl fumarate.

2. A sublimable composition comprising 1 to 25 parts by weight of adamantane, 99 to 75 parts by weight of endo-trimethylenenorbornane and 0.5 to 90 parts by weight of trioxymethylene.

3. A sublimable composition comprising 5 to 95 parts by weight of adamantane, 95 to 5 parts by weight of cyclododecane, and 0.1 to 40 parts by weight of dimethyl fumarate.

4. A sublimable composition comprising 5 to 95 parts by weight of adamantane, 95 to 5 parts by weight of cyclododecane and 0.1 to 10 parts by weight of benzoic acid.

5. A sublimable composition comprising 99.9 to 70 parts by weight of endo-trimethylenenorbornane, and 0.1 to 30 parts by weight of dimethyl fumarate.

6. A sublimable composition comprising 99.9 to 40 parts by weight of cyclododecane and 0.1 to 60 parts by weight of dimethyl fumarate.

7. A sublimable composition comprising (i) a sublimable hydrocarbon comprising at least one hydrocarbon selected from the group consisting of adamantane, endo-trimethylenenorbornane, cyclododecane, norbornane and trimethylnorbornane and (ii) a sublimable polar compound comprising at least one compound selected from the group consisting of dimethyl fumarate, benzoic acid, trioxymethylene, cumarin, p-dichlorobenzene, $\epsilon$-caprolactam 1,4-cyclohexanediol, phthalide, lactide and triisopropyltrioxane.

8. The sublimable composition of claim 7 wherein said sublimable hydrocarbon is adamantane in an amount between 80 and 10 parts by weight of adamantane per 20 to 90 parts by weight of said sublimable polar compound.

9. The sublimable composition of claim 7 wherein said sublimable hydrocarbon is adamantane in an amount between 50 and 10 parts by weight of adamantane per 50 to 90 parts by weight of said sublimable polar compound.

10. The sublimable composition of claim 9 wherein said adamantane is in an amount sufficient to form the continuous phase and said polar compound is present in a discontinuous phase carried by said continuous phase.

11. The sublimable composition of claim 7 wherein said sublimable hydrocarbon is in an amount sufficient to form the continuous phase and said polar compound is present in a discontinuous phase carried by said continuous phase.

12. The sublimable composition of claim 7 or 10 which also contains a perfume.

13. The sublimable composition of claim 7, which also contains an antioxidant.

14. The sublimable composition of claim 13, wherein the antioxidant is composed of one or more materials selected from the group consisting of hydroquinone monomethyl ether, hydroquinone and resorcine.

15. The sublimable composition of claim 7 or 10 which also contains a moth-proofing agent.

16. The sublimable composition of claim 7 or 10 which also contains an insecticide.

17. The sublimable composition of claim 7 or 10 which also contains a rust preventive.

18. The sublimable compostion of claim 7 or 10 which also contains a mold-proofing agent.

19. The sublimable composition of claim 7 or 10 which also contains a preservative.

* * * * *